(12) United States Patent
Epstein et al.

(10) Patent No.: US 7,375,185 B2
(45) Date of Patent: May 20, 2008

(54) CARDIAC MYOSIN LIGHT CHAIN KINASE POLYPEPTIDE, ENCODING NUCLEIC ACID, AND METHODS OF USE

(75) Inventors: Neal D. Epstein, Chevy Chase, MD (US); Shahin Hassanzadeh, Manassas, VA (US); Steven Winitsky, Bethesda, MD (US); Julien S. Davis, Baltimore, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 492 days.

(21) Appl. No.: 10/380,236

(22) PCT Filed: Sep. 12, 2001

(86) PCT No.: PCT/US01/28639

§ 371 (c)(1),
(2), (4) Date: Sep. 25, 2003

(87) PCT Pub. No.: WO02/24889

PCT Pub. Date: Mar. 28, 2002

(65) Prior Publication Data

US 2004/0126860 A1    Jul. 1, 2004

Related U.S. Application Data

(60) Provisional application No. 60/232,456, filed on Sep. 13, 2000, provisional application No. 60/232,246, filed on Sep. 12, 2000.

(51) Int. Cl.
*C07K 1/00* (2006.01)

(52) U.S. Cl. .................. 530/350; 530/300; 435/7.1; 514/2; 514/12

(58) Field of Classification Search .............. None
See application file for complete search history.

(56) References Cited

U.S. PATENT DOCUMENTS 6,730,491 B2 * 5/2004 Kapeller-Libermann et al. .............. 435/15

FOREIGN PATENT DOCUMENTS

| EP | 0 357 856 | 3/1990 |
| WO | WO 01/38503 | 5/2001 |
| WO | WO 01/64905 | 9/2001 |
| WO | WO 01/85767 | 11/2001 |
| WO | WO 01/96547 | 12/2001 |

OTHER PUBLICATIONS

Janko P, On the activation mechanism of cardiac myosin light chain kinase, 1982, Hormones and Cell Regulation, vol. 6, pp. 27-35.*
Seffernick et al., J. Bacteriology, vol. 183, pp. 2405-2410, 2001.*
Wells, Biochemistry, vol. 29, pp. 8509-8517, 1990.*
Aoki et al., *Nature Medicine* 6(2):183-188 (2000).
Gallagher et al., *Journal of Muscle Research and Cell Mobility* 18:1-16 (1997).
GenBank Accession No. AL160175 (Mar. 13, 2000).
GenBank Accession No. AF325649 (Mar. 9, 2001).
Herring et al., *Journal of Biological Chemistry* 265(3):1724-1730 (1990).
Herring et al., *Am. J. Physiol Cell Physiol* 279:C1656-C1664 (2000).
Liu et al., *J. Mol Cell Cardiol* 27:2613-2621 (1995).
Poetter et al., *Nature Genetics* 13:63-69 (1996).
Roush et al., *The Journal of Biological Chemistry* 263(11):10510-10516 (1988).
Vemuri et al., *Proc. Natl. Acad. Sci. USA* 96:1048-1053 (1999).

* cited by examiner

*Primary Examiner*—Hope Robinson
(74) *Attorney, Agent, or Firm*—Klarquist Sparkman, LLP

(57) ABSTRACT

The present disclosure provides a cDNA, protein sequence, and genomic structure of the human cardiac isoform of myosin light chain kinase (cMLCK), and describes mutations in the cMLCK gene that are associated with cardiac dysfunction. Methods are provided for identifying individuals who can harbor mutations in the cMLCK gene, or carry alleles that can predisposed them to cardiac dysfunction. Disclosed also is a significant role for cMLCK in modulating cardiac contractility. The cMLCK protein is shown herein to reduce the amplitude of stretch activation and increase the tension production, a property of muscle which has heretofore had an unknown role in cardiac contraction. Moreover, the cMLCK protein is shown to be regionally distributed in the heart, thereby having differential effects on contractility and stretch activation. Methods herein are provided to exploit this effect of cMLCK, to treat individuals who have or are prone to cardiac dysfunction. In addition, methods are provided to identify agents that modulate cMLCK activity, thereby having potential therapeutic importance in the treatment of cardiac dysfunction.

10 Claims, No Drawings

SEQUENCE LISTING

<160> NUMBER OF SEQ ID NOS: 26

<210> SEQ ID NO 1
<211> LENGTH: 1791
<212> TYPE: DNA
<213> ORGANISM: Homo sapiens -continued

<400> SEQUENCE: 1

```
atggcgacag aaaatggagc agttgagctg ggaattcaga acccatcaac agacaaggca      60
cctaaaggtc ccacaggtga agacccctg gctgcaggga agaccctgg ccccccagac       120
ccaaagaaag ctccggatcc acccaccctg aagaagatg ccaaagcccc tgcctcagag      180
aaaggggatg taccctggc caaccctca actagcagcc aaggcccca aggagagggt        240
gacagggcg ggggccgc ggagggcagt gctgggcccc ggcagccct gccccagcag         300
actgcgacac ctgagaccag cgtcaagaag cccaaggctg agcagggagc ctcaggcagc     360
caggatcctg aaagcccag ggtgggcaag aaggcagcag agggccaagc agcagccagg      420
aggggctcac ctgcctttct gcatagcccc agctgtcctg ccatcatctc cagttctgag     480
aagctgctgg ccaagaagcc cccaagcgag gcatcagagc tcacctttga aggggtgccc    540
atgacccaca gccccacgga tcccaggcca gccaaggcag aagaaggaaa gaacatcctg    600
gcagagagcc agaaggaagt gggagagaaa accccaggcc aggctggcca ggctaagatg    660
caaggggaca cctcgagggg gattgagttc caggctgttc cctcagagaa atccgaggtg    720
gggcaggccc tctgtctcac agccagggag gaggactgct tccagatttt ggatgattgc    780
ccgccacctc cggccccctt ccctcaccgc atggtggagc tgaggaccgg aatgtcagc     840
agtgaattca gtatgaactc caaggaggcg ctcgagggtg gcaagtttgg ggcagtctgt    900
acctgcatgg agaaagccac aggcctcaag ctggcagcca ggtcatcaa gaaacagact     960
cccaaagaca aggaaatggt gttgctggag attgaggtca tgaaccagct gaaccaccgc   1020
aatctgatcc agctgtatgc agccatcgag actccgcatg agatcgtcct gttcatggag   1080
tacatcgagg cggagagct cttcgagagg attgtggatg aggactacca tctgaccgag   1140
gtggacacca tggtgtttgt caggcagatc tgtgacggga tcctcttcat gcacaagatg   1200
agggttttgc acctggacct caagccagag aacatcctgt gtgtcaacac caccgggcat   1260
ttggtgaaga tcattgactt tggcctggca cggaggtata accccaacga aagctgaag    1320
gtgaactttg gaccccaga gttcctgtca cctgaggtgg tgaattatga ccaaatctcc   1380
gataagacag acatgtggag tatgggggtg atcacctaca tgctgctgag cggcctctcc   1440
cccttcctgg gagatgatga cacagagacc ctaaacaacg ttctatctgg caactggtac   1500
tttgatgaag agacctttga ggccgtatca gacgaggcca agactttgt ctccaacctc   1560
atcgtcaagg accagagggc ccggatgaac gctgcccagt gtctcgccca tccctggctc   1620
aacaacctgg cggagaaagc caaacgctgt aaccgacgcc ttaagtccca gatcttgctt   1680
aagaaatacc tcatgaagag gcgctggaag aaaaacttca ttgctgtcag cgctgccaac   1740
cgcttcaaga agatcagcag ctcggggca ctgatggctc tgggggtctg a            1791
```

<210> SEQ ID NO 2
<211> LENGTH: 596
<212> TYPE: PRT
<213> ORGANISM: Homo sapiens

<400> SEQUENCE: 2

```
Met Ala Thr Glu Asn Gly Ala Val Glu Leu Gly Ile Gln Asn Pro Ser
1               5                   10                  15

Thr Asp Lys Ala Pro Lys Gly Pro Thr Gly Glu Arg Pro Leu Ala Ala
            20                  25                  30

Gly Lys Asp Pro Gly Pro Pro Asp Pro Lys Lys Ala Pro Asp Pro Pro
        35                  40                  45
```

-continued

```
Thr Leu Lys Lys Asp Ala Lys Ala Pro Ala Ser Glu Lys Gly Asp Gly
 50                  55                  60

Thr Leu Ala Gln Pro Ser Thr Ser Ser Gln Gly Pro Lys Gly Glu Gly
 65                  70                  75                  80

Asp Arg Gly Gly Gly Pro Ala Glu Gly Ser Ala Gly Pro Pro Ala Ala
                 85                  90                  95

Leu Pro Gln Gln Thr Ala Thr Pro Glu Thr Ser Val Lys Lys Pro Lys
            100                 105                 110

Ala Glu Gln Gly Ala Ser Gly Ser Gln Asp Pro Gly Lys Pro Arg Val
        115                 120                 125

Gly Lys Lys Ala Ala Glu Gly Gln Ala Ala Arg Arg Gly Ser Pro
130                 135                 140

Ala Phe Leu His Ser Pro Ser Cys Pro Ala Ile Ile Ser Ser Ser Glu
145                 150                 155                 160

Lys Leu Leu Ala Lys Lys Pro Pro Ser Glu Ala Ser Glu Leu Thr Phe
                165                 170                 175

Glu Gly Val Pro Met Thr His Ser Pro Thr Asp Pro Arg Pro Ala Lys
            180                 185                 190

Ala Glu Glu Gly Lys Asn Ile Leu Ala Glu Ser Gln Lys Glu Val Gly
        195                 200                 205

Glu Lys Thr Pro Gly Gln Ala Gly Gln Ala Lys Met Gln Gly Asp Thr
    210                 215                 220

Ser Arg Gly Ile Glu Phe Gln Ala Val Pro Ser Glu Lys Ser Glu Val
225                 230                 235                 240

Gly Gln Ala Leu Cys Leu Thr Ala Arg Glu Glu Asp Cys Phe Gln Ile
                245                 250                 255

Leu Asp Asp Cys Pro Pro Pro Ala Pro Phe Pro His Arg Met Val
            260                 265                 270

Glu Leu Arg Thr Gly Asn Val Ser Ser Glu Phe Ser Met Asn Ser Lys
        275                 280                 285

Glu Ala Leu Gly Gly Gly Lys Phe Gly Ala Val Cys Thr Cys Met Glu
    290                 295                 300

Lys Ala Thr Gly Leu Lys Leu Ala Ala Lys Val Ile Lys Lys Gln Thr
305                 310                 315                 320

Pro Lys Asp Lys Glu Met Val Leu Leu Glu Ile Glu Val Met Asn Gln
                325                 330                 335

Leu Asn His Arg Asn Leu Ile Gln Leu Tyr Ala Ala Ile Glu Thr Pro
            340                 345                 350

His Glu Ile Val Leu Phe Met Glu Tyr Ile Glu Gly Gly Glu Leu Phe
        355                 360                 365

Glu Arg Ile Val Asp Glu Asp Tyr His Leu Thr Glu Val Asp Thr Met
    370                 375                 380

Val Phe Val Arg Gln Ile Cys Asp Gly Ile Leu Phe Met His Lys Met
385                 390                 395                 400

Arg Val Leu His Leu Asp Leu Lys Pro Glu Asn Ile Leu Cys Val Asn
                405                 410                 415

Thr Thr Gly His Leu Val Lys Ile Ile Asp Phe Gly Leu Ala Arg Arg
            420                 425                 430

Tyr Asn Pro Asn Glu Lys Leu Lys Val Asn Phe Gly Thr Pro Glu Phe
        435                 440                 445

Leu Ser Pro Glu Val Val Asn Tyr Asp Gln Ile Ser Asp Lys Thr Asp
450                 455                 460
```

```
Met Trp Ser Met Gly Val Ile Thr Tyr Met Leu Leu Ser Gly Leu Ser
465                 470                 475                 480

Pro Phe Leu Gly Asp Asp Thr Glu Thr Leu Asn Asn Val Leu Ser
            485                 490                 495

Gly Asn Trp Tyr Phe Asp Glu Glu Thr Phe Glu Ala Val Ser Asp Glu
                500                 505                 510

Ala Lys Asp Phe Val Ser Asn Leu Ile Val Lys Asp Gln Arg Ala Arg
        515                 520                 525

Met Asn Ala Ala Gln Cys Leu Ala His Pro Trp Leu Asn Asn Leu Ala
        530                 535                 540

Glu Lys Ala Lys Arg Cys Asn Arg Arg Leu Lys Ser Gln Ile Leu Leu
545                 550                 555                 560

Lys Lys Tyr Leu Met Lys Arg Arg Trp Lys Lys Asn Phe Ile Ala Val
                565                 570                 575

Ser Ala Ala Asn Arg Phe Lys Lys Ile Ser Ser Ser Gly Ala Leu Met
            580                 585                 590

Ala Leu Gly Val
        595

<210> SEQ ID NO 3
<211> LENGTH: 384
<212> TYPE: DNA
<213> ORGANISM: Homo sapiens
<220> FEATURE:
<221> NAME/KEY: exon
<222> LOCATION: (214)..(265)
<223> OTHER INFORMATION: Exon 1

<400> SEQUENCE: 3
gactgctcct gagcagccgc tggagacaga cggcaaccag gttggcccct ctttgctcca     60
ggtacctctc tcccccctcag ttagcaggct cggcttcctg tctcactgca gccagacgag   120
aggggaaatt ggacagcctg ccacactcca ctcttgtttc tgcagctaga aagacttgag    180
ttagacaagc agaagcacac gcctccctac ctc atg gcg aca gaa aat gga gca    234
                                     Met Ala Thr Glu Asn Gly Ala
                                     1               5 gtt gag ctg gga att cag aac cca tca aca g gtgccaagct ggggcaggag      285
Val Glu Leu Gly Ile Gln Asn Pro Ser Thr
        10                  15 atggagggag gagcttggga aggggggttt tgaatccagg actgggcaag gttccctcag    345
tgggagttct gtgccccagc cttgtttgca tggtgcacg                           384

<210> SEQ ID NO 4
<211> LENGTH: 533
<212> TYPE: DNA
<213> ORGANISM: Homo sapiens
<220> FEATURE:
<221> NAME/KEY: misc_feature
<222> LOCATION: (40)..(460)
<223> OTHER INFORMATION: Exon 2

<400> SEQUENCE: 4
aaaggagggt ggatcctgat ggtgttctca cctctgcaga caaggcacct aaaggtccca     60
caggtgaaag accctggct gcagggaaag accctggccc ccagacccca agaaagctc     120 cggatccacc caccctgaag aaagatgcca agcccctgc ctcagagaaa ggggatggta    180
ccctggccca accctcaact agcagccaag gccccaaagg agagggtgac aggggcgggg   240
ggcccgcgga gggcagtgct ggccccccgg cagccctgcc ccagcagact gcgacacctg   300
```

```
agaccagcgt caagaagccc aaggctgagc agggagcctc aggcagccag gatcctggaa      360
agcccagggt gggcaagaag gcagcagagg gccaagcagc agccaggagg ggctcacctg      420
cctttctgca tagccccagc tgtcctgcca tcatctccag gtgaatatcc cctcctggga      480
gtggggaggg gtcctgtggt tctgtcccta ggggtcctgc ttaattccct tgt             533
```

```
<210> SEQ ID NO 5
<211> LENGTH: 409
<212> TYPE: DNA
<213> ORGANISM: Homo sapiens
<220> FEATURE:
<221> NAME/KEY: misc_feature
<222> LOCATION: (33)..(331)
<223> OTHER INFORMATION: Exon 3

<400> SEQUENCE: 5
gcgggcttca cctctgtgtt ctcaccttct agttctgaga agctgctggc caagaagccc      60
ccaagcgagg catcagagct cacctttgaa ggggtgccca tgacccacag ccccacggat     120
cccaggccag ccaaggcaga agaaggaaag aacatcctgg cagagagcca gaaggaagtg     180
ggagagaaaa ccccaggcca ggctggccag gctaagatgc aagggacaca ctcgagggg      240 attgagttcc aggctgttcc ctcagagaaa tccgaggtgg ggcaggccct ctgtctcaca     300
gccagggagg aggactgctt ccagattttg ggtaggccag gggcaggtgg gggctggggc     360
tgctctgggg ccaggggag gaaggggct gtcagtccca agtctacct                   409
```

```
<210> SEQ ID NO 6
<211> LENGTH: 219
<212> TYPE: DNA
<213> ORGANISM: Homo sapiens
<220> FEATURE:
<221> NAME/KEY: misc_feature
<222> LOCATION: (66)..(171)
<223> OTHER INFORMATION: Exon 4

<400> SEQUENCE: 6
tggtgccaag gggaatcctc agcagcccct ggcactgacc atgagggctg tgctctgtcc      60
cccagatgat tgcccgccac ctccggcccc cttccctcac cgcatggtgg agctgaggac     120
cgggaatgtc agcagtgaat tcagtatgaa ctccaaggag gcgctcggag ggtgagatct     180
gggaccccag ctgggcactc atggacagag agcacaccg                            219
```

```
<210> SEQ ID NO 7
<211> LENGTH: 229
<212> TYPE: DNA
<213> ORGANISM: Homo sapiens
<220> FEATURE:
<221> NAME/KEY: misc_feature
<222> LOCATION: (39)..(132)
<223> OTHER INFORMATION: Exon 5

<400> SEQUENCE: 7
cttggggtcc cctaacttac agcctcttct ctttccagtg gcaagtttgg ggcagtctgt      60
acctgcatgg agaaagccac aggcctcaag ctggcagcca aggtcatcaa gaaacagact     120
cccaaagaca aggtagtgag gttgcggggg tggtggctgc ccaggatggg gagggatcc      180 ttggagtagg gcacctctcg cctccctcca ccagcagctg ctgaacctg                 229
```

```
<210> SEQ ID NO 8
<211> LENGTH: 201
<212> TYPE: DNA
<213> ORGANISM: Homo sapiens
```

```
<220> FEATURE:
<221> NAME/KEY: misc_feature
<222> LOCATION: (27)..(136)
<223> OTHER INFORMATION: Exon 6

<400> SEQUENCE: 8
gtacccttta cttccctggt ccccaggaaa tggtgttgct ggagattgag gtcatgaacc      60
agctgaacca ccgcaatctg atccagctgt atgcagccat cgagactccg catgagatcg     120
tcctgttcat ggagtagtga gtggccgaag tagtggtagg ggctgggtgg gggtaccacc     180
aggcacggag caagccgtgg a                                               201

<210> SEQ ID NO 9
<211> LENGTH: 212
<212> TYPE: DNA
<213> ORGANISM: Homo sapiens
<220> FEATURE:
<221> NAME/KEY: misc_feature
<222> LOCATION: (45)..(186)
<223> OTHER INFORMATION: Exon 7

<400> SEQUENCE: 9
taccaccagg cacggagcaa gccgtggagg ggtctgtgca cgcacatcga gggcggagag      60
ctcttcgaga ggattgtgga tgaggactac catctgaccg aggtggacac catggtgttt     120
gtcaggcaga tctgtgacgg gatcctcttc atgcacaaga tgagggtttt gcacctggac     180
ctcaaggtac cagactgggg cctcctggga ag                                   212

<210> SEQ ID NO 10
<211> LENGTH: 168
<212> TYPE: DNA
<213> ORGANISM: Homo sapiens
<220> FEATURE:
<221> NAME/KEY: misc_feature
<222> LOCATION: (38)..(108)
<223> OTHER INFORMATION: Exon 8

<400> SEQUENCE: 10
tgcagaggcc cacccaggcc accccctttc tcctcagcca gagaacatcc tgtgtgtcaa      60
caccaccggg catttggtga agatcattga ctttggcctg gcacggaggt accacctggg     120
tgggtgggga gggcaagaca agcctctgag ttggcagggg caggggtg                  168

<210> SEQ ID NO 11
<211> LENGTH: 200
<212> TYPE: DNA
<213> ORGANISM: Homo sapiens
<220> FEATURE:
<221> NAME/KEY: misc_feature
<222> LOCATION: (36)..(164)
<223> OTHER INFORMATION: Exon 9

<400> SEQUENCE: 11
ggactgtgct ctcagccctt ggtctcaccc ccagggtata accccaacga gaagctgaag      60
gtgaactttg gaccccaga gttcctgtca cctgaggtgg tgaattatga ccaaatctcc     120
gataagacag acatgtggag tatgggggtg atcacctaca tgctgtgagc acccaggagg     180
gtcgtgttta tggggttggt                                                 200

<210> SEQ ID NO 12
<211> LENGTH: 261
<212> TYPE: DNA
<213> ORGANISM: Homo sapiens
<220> FEATURE:
```

```
<221> NAME/KEY: misc_feature
<222> LOCATION: (45)..(197)
<223> OTHER INFORMATION: Exon 10

<400> SEQUENCE: 12
cctccaatct cacctccctg ccccctgcta tcccctccct ctaggctgag cggcctctcc      60
cccttcctgg gagatgatga cacagagacc ctaaacaacg ttctatctgg caactggtac     120
tttgatgaag agacctttga ggccgtatca gacgaggcca agactttgt ctccaacctc      180 atcgtgaagg accagaggtg aggctcaccc cagaacctga actgtatgtg tgcaagctta     240
gtgtgtctga gtgctggcag g                                              261

<210> SEQ ID NO 13
<211> LENGTH: 229
<212> TYPE: DNA
<213> ORGANISM: Homo sapiens
<220> FEATURE:
<221> NAME/KEY: misc_feature
<222> LOCATION: (28)..(160)
<223> OTHER INFORMATION: Exon 11

<400> SEQUENCE: 13
ccacgtcacc atgctgcctc tcccccaggc ccggatgaac gctgcccagt gtctcgccca      60
tccctggctc aacaacctgg cggagaaagc caaacgctgt aaccgacgcc ttaagtccca     120
gatcttgctt aagaaatacc tcatgaagag gcgctggaag gtaccgctgg attcggggtg     180
gggagggagg gcttgctagt gggaagagct cctggtgcca gatcccagc                 229

<210> SEQ ID NO 14
<211> LENGTH: 167
<212> TYPE: DNA
<213> ORGANISM: Homo sapiens
<220> FEATURE:
<221> NAME/KEY: misc_feature
<222> LOCATION: (46)..(126)
<223> OTHER INFORMATION: Exon 12

<400> SEQUENCE: 14
ccctgccctg gtgttgactg ggactccctc tcttctgccc tctagaaaaa cttcattgct      60
gtcagcgctg ccaaccgctt caagaagatc agcagctcgg gggcactgat ggctctgggg     120
gtctgagccc tgggcgcagc tgaagcctgg acgcagccac acagtgg                   167

<210> SEQ ID NO 15
<211> LENGTH: 14
<212> TYPE: PRT
<213> ORGANISM: Homo sapiens

<400> SEQUENCE: 15

Gly Ala Asn Ser Asn Val Phe Gly Ala Asn Ser Asn Val Phe
1               5                   10

<210> SEQ ID NO 16
<211> LENGTH: 14
<212> TYPE: PRT
<213> ORGANISM: Homo sapiens

<400> SEQUENCE: 16

Gly Gly Ala Asn Ser Asn Val Phe Ser Met Phe Glu Gln Thr
1               5                   10

<210> SEQ ID NO 17
<211> LENGTH: 17
```

```
<212> TYPE: DNA
<213> ORGANISM: Homo sapiens

<400> SEQUENCE: 17
atggcgacag aaaatgg                                                 17

<210> SEQ ID NO 18
<211> LENGTH: 17
<212> TYPE: DNA
<213> ORGANISM: Homo sapiens

<400> SEQUENCE: 18
tcagaccccc agagcca                                                 17

<210> SEQ ID NO 19
<211> LENGTH: 20
<212> TYPE: DNA
<213> ORGANISM: Artificial Sequence
<220> FEATURE:
<223> OTHER INFORMATION: rabbit skeletcal muscle

<400> SEQUENCE: 19
tgatccagct gtacgcagcc                                              20

<210> SEQ ID NO 20
<211> LENGTH: 19
<212> TYPE: DNA
<213> ORGANISM: Artificial Sequence
<220> FEATURE:
<223> OTHER INFORMATION: rabbit skeletal muscle

<400> SEQUENCE: 20
cttgaggtcc aggtgcagc                                               19

<210> SEQ ID NO 21
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (8)..(8)
<223> OTHER INFORMATION: n = a, g, or t
<220> FEATURE:
<221> NAME/KEY: misc_feature
<222> LOCATION: (15)..(15)
<223> OTHER INFORMATION: n = a, g, or t
<220> FEATURE:
<221> NAME/KEY: misc_feature
<222> LOCATION: (20)..(20)
<223> OTHER INFORMATION: n = a, g, or t

<400> SEQUENCE: 21
aggtccangt gcagnacccn ca                                           22

<210> SEQ ID NO 22
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: n = c or g

<400> SEQUENCE: 22
```

-continued

```
cgtnctgttc atggagt                                                    17

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ccacggcttg ctccgtgcct                                                 20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
atcgagactc cgcatgagat                                                 20

<210> SEQ ID NO 25
<211> LENGTH: 56
<212> TYPE: PRT
<213> ORGANISM: Artificial Sequence
<220> FEATURE:
<223> OTHER INFORMATION: peptide containing C-terminal of cMLCK residues

<400> SEQUENCE: 25

Asn Asn Leu Ala Glu Lys Ala Lys Arg Cys Asn Arg Arg Leu Lys Ser
1               5                   10                  15

Gln Ile Leu Leu Lys Lys Tyr Leu Met Lys Arg Arg Trp Lys Lys Asn
            20                  25                  30

Phe Ile Ala Val Ser Ala Ala Asn Arg Phe Lys Lys Ile Ser Ser Ser
        35                  40                  45

Gly Ala Leu Met Ala Leu Gly Val
    50                  55

<210> SEQ ID NO 26
<211> LENGTH: 7
<212> TYPE: PRT
<213> ORGANISM: Artificial Sequence
<220> FEATURE:
<223> OTHER INFORMATION: peptide

<400> SEQUENCE: 26

Gly Ala Asn Ser Asn Val Phe
1               5
```

CARDIAC MYOSIN LIGHT CHAIN KINASE POLYPEPTIDE, ENCODING NUCLEIC ACID, AND METHODS OF USE

PRIORITY CLAIM

This is a § 371 U.S. national stage of PCT/US01/28639, filed Sep. 12, 2001, which was published in English under PCT Article 21(2), and claims the benefit of U.S. Provisional Application No. 60/232,246, filed Sep. 12, 2000 and U.S. Provisional Application No. 60/232,456, filed Sep. 13, 2000.

BACKGROUND

The function of a mammal's circulatory system—its heart, lungs, blood vessels and red blood cells—is to provide oxygen and nutrients to every cell. The heart's role is to pump oxygenated red blood cells to the tissues, to receive deoxygenated blood from the tissues, and to pump deoxygenated blood to the lungs where it can again take up oxygen. Heart failure can be viewed as the failure to fulfill this role.

Heart failure affects more than 2 million Americans, and is a major cause of illness, hospitalization, and death around the world. Currently available therapies includes medications such as digoxin and angiotensin converting enzyme inhibitors, but these have had limited impact on morbidity and mortality. Left ventricular assist devices show promise, but remain experimental. Cardiac transplantation is limited by a shortage of available hearts, and the need for permanent immunosuppression. Thus, improved therapies for heart failure are needed.

To develop improved therapies for heart failure, a more complete understanding of the heart's normal operation is needed. With this more complete understanding, specific aspects of heart function can be targeted for pharmacologic therapy, gene therapy, and other novel therapeutic approaches.

Many basic facts about heart function are known. The heart is largely made up of cardiac muscle, or myocardium. The myocardium mediates the heart's pumping function by automatically contracting and relaxing in a cyclical manner. The contraction drives the blood forward, while the relaxation phase creates negative pressure that helps the heart to fill with blood. This alternation of myocardial contraction and relaxation is termed the cardiac cycle.

In pumping blood, the vertebrate heart takes advantage of the increased efficiency of wringing compared to compression. Just as both hands rotate in opposite directions during the squeeze, the base of the heart rotates in the clockwise direction as the apex rotates counter-clockwise. An advantage of these mechanics is the reduction of chamber volume and consequential decrease in wall stress. The orientations of many cardiac muscle bundles facilitate the wringing as well as compressing forces.

The molecular motor that drives contraction of cardiac muscle is myosin. The role of myosin is to transduce chemical energy into movement by hydrolyzing the high-energy phosphodiester bond of ATP.

Myosin is a large protein made up of three subunits, the myosin heavy chain and two myosin light chains termed essential light chain (ELC) and regulatory light chain (RLC). The myosin heavy chain is an elongated molecule with a filamentous tail and a globular head. A "neck" region lies between the tail and head. The tails self-assemble into filaments, with the myosin head extending outward from the filament. These myosin-containing filaments are termed thick filaments. They interact with thin filaments, which contain actin polymers. The actin polymers activate the ATPase activity found in the myosin head. Movement is generated when the myosin heads: (1) bind to actin filaments; (2) hydrolyze ATP, thereby generating a lever like motion at the myosin neck; and (3) detach from sites on the actin-containing thin filament. The constant repetition of this cycle pushes the thin filament past the thick filaments, thereby generating differential motion. Multiplied over millions of highly organized cardiac cells, the result is a highly coordinated cycle of contraction and relaxation.

The trigger for cardiac contraction is a transient rise in the intracellular level of calcium. The actin-containing thin filament binds an additional protein complex called troponin. In the absence of calcium, troponin interferes with the actin-myosin interaction. However, the troponin complex contains a high-affinity calcium binding protein which binds calcium, thereby triggering a movement of the complex which allows actin and myosin to interact productively. Cardiomyocytes contain intracellular calcium stores that rapidly release calcium and take it back, thereby promoting the cycle of contraction and relaxation.

The neck region of the myosin heavy chain is supported by the two myosin light chains. The precise role of these myosin light chains in cardiac muscle has remained elusive. In smooth muscle (found in blood vessels and internal organs, for example) the RLC plays a critical regulatory role: for contraction to proceed, the RLC must be phosphorylated by a calcium-activated enzyme called myosin light chain kinase (MLCK). In the absence of MLCK-mediated RLC phosphorylation, smooth muscle myosin ATPase activity is not activated, and the muscle remains relaxed.

In stark contrast to smooth muscle, cardiac RLC phosphorylation has little effect on myosin ATPase activity. A modest increase in sensitivity to calcium has been described in isolated, chemically "skinned" (i.e., outer membranes removed) fibers in vitro, but this observation is of doubtful in vivo significance. Nevertheless, a phosphorylatable serine homologous to smooth muscle RLC has been preserved throughout evolution, and the reasons for this conservation have remained a mystery.

Further study of a possible role for cardiac RLC phosphorylation has been significantly hampered by the lack of sequence information about the cardiac form of MLCK. What is needed is the complete cDNA sequence of cardiac MLCK in humans and other mammalian species, as well as the deduced amino acid sequence and genomic sequence.

Indirect flight muscle (IFM) of insects has the same basic contractile apparatus as mammalian cardiac muscle: a myosin based thick filament comprised of myosin heavy and light chains; and an actin-containing thin filament activated by calcium binding to troponin. However, IFM must contract and relax 150 times per second during flight. It would be energetically wasteful to regulate this extraordinarily rapid cycle exclusively through release and reuptake of calcium from intracellular stores. Thus, IFM has evolved to accentuate and exploit a property of muscle contraction termed stretch activation.

The stretch activation response of IFM manifests itself as a "delayed tension" when an activated muscle fiber is subjected to a quick stretch When tension is monitored as a function of time (for example, by attaching an isolated muscle to a sensitive force transducer), and IFM is quickly stretched, an immediate increase in tension is observed which rapidly decays. This immediate tension increase is mediated by elastic recoil. In IFM, there is a second, delayed rise in tension which is defined as stretch activation. This response has been shown to be a critical component of IFM function, since it contributes substantially to oscillatory power output. Drosophila mutants lacking stretch activation have no ability to fly.

The role of stretch activation can be likened to pushing a child on a swing: when a swing is at the rear of its arc, it has zero velocity and is about to be pulled forward by gravity. A properly timed push is a very efficient way to enhance the forward swinging force. In IFM, stretch activation corresponds to the push Stretch activation is intimately related to another important property of IFM, namely resonant frequency. As in the swing metaphor, the swing arc has a predictable frequency, and will return to the pushing individual at a particular time. This predictable frequency is the swing's resonant frequency. The individual must time the push to the resonant frequency. Such precise timing will maximally enhance the swinging motion's amplitude with the least amount of effort. An improperly timed push will not enhance the amplitude, and may in fact work against the swinging motion. Similarly, the resonant frequency of stretch activation in IFM must be precisely matched to the cycle of muscle contraction and relaxation.

Several mutations in human cardiac ELCs and RLCs are associated with an unusual inherited disease of cardiac muscle (cardiomyopathy) termed mid-cavitary ventricular hypertrophy (MCVH; Poetter et al., Nature Genetics 13: 63-69, 1996). In its fully developed form, MCVH is characterized by massive overgrowth or hypertrophy largely confined to the center of the left ventricle—the papillary muscles, and adjacent interventricular septum and left ventricular free walls. The physiologic basis for this unusual, regionally confined hypertrophy is unknown. Interestingly, however, when a mutant human cardiac ELC is expressed in transgenic mice, the mice develop regional hypertrophy indistinguishable from human MCVH. Papillary muscles removed from the hearts of these transgenic mice show altered stretch activation, even before the hypertrophy develops (Vermuri et al., PNAS 96: 1048-1053, 1999). The alteration included a significantly increased resonant frequency.

It would be helpful to determine whether stretch activation has a significant role in mammalian cardiac muscle, and to develop new therapies for heart disease based on modulation of stretch activation. Improved and more comprehensive methods of identifying individuals at risk of developing cardiac dysfunctions, such as cardiomyopathy, would also be beneficial.

SUMMARY OF THE DISCLOSURE

The foregoing problems are addressed by the present invention, wherein the cardiac myosin light chain kinase (cMLCK) gene of humans has been identified and cloned, the sequence of the cDNA and protein determined, and the role of cMLCK in cardiac contraction clarified. It is shown herein that cardiac myosin light chain kinase is regionally distributed in the heart, and is most active at the apex and base of the heart. It is further shown that cMLCK phosphorylation of human cardiac RLC surprisingly decreases the amplitude of the stretch activation response, thereby reducing the impact of stretch activation on cardiac contraction.

The foregoing and other objects, features, and advantages of the compositions and methods disclosed herein will become more apparent from the following detailed description of several embodiments, which proceeds with reference to the accompanying sequence listing.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand. In the accompanying sequence listing:

SEQ ID NO: 1 show the nucleotide sequence of the cMLCK cDNA;

SEQ ID NO: 2 shows the amino acid sequence of the cMLCK protein;

SEQ ID NOs: 3-14 show exons 1-12 of the cMCLK, with surrounding intron sequences.

SEQ ID NO: 15 shows the sequence of the peptide used to generate antibody to the phosphorylated form of human RLC.

SEQ ID NO: 16 shows the amino acid sequence of a human cardiac MLC peptide.

SEQ ID NOs: 17-24 are primer sequences.

SEQ ID NO: 25 is the c-terminal 46 residues of cMLCK.

SEQ ID NO: 26 is a peptide for producing antibodies.

DETAILED DESCRIPTION

Unless otherwise noted, technical terms are used according to conventional usage. Definitions of common terms in molecular biology may be found in Benjamin Lewin, Genes VII, published by Oxford University Press, 1999; Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments disclosed herein, the following list of abbreviations and definition of terms is provided:

I. Abbreviations and Definitions
  A. Abbreviations
  ATP: Adenosine triphosphate
  ELC: essential myosin light chain; also referred to as MLC1
  HCM: hypertrophic cardiomyopathy
  MVC: mid-venticular cavitary hypertrophy
  cMLCK: cardiac isoform of myosin light chain kinase
  MLCK: myosin light chain kinase
  MLC: myosin light chain
  RLC: regulatory myosin light chain, also referred to as MLC2
  RLC-P: phosphorylated form of RLC, after phosphorylation by MLCK.
  IFM: indirect flight muscle of insects
  P1: P1-derived artificial chromosome
  PCR: polymerase chain reaction
  B. Definitions
  Unless otherwise noted, technical terms are used according to conventional usage. Definitions of common terms in molecular biology may be found in Benjamin Lewin, *Genes VI*, published by Oxford University Press, 1997 (ISBN 0-19-857778-8); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Amplification: When used in reference to a nucleic acid, techniques that increases the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Antisense, Sense, and Antigene: Double-stranded DNA (dsDNA) has two strands, a 5'->3' strand, referred to as the plus strand, and a 3'->5' strand (the reverse compliment), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Cardiac: pertaining to the heart.

Cardiac myosin light chain kinase gene: A novel gene that codes for a cardiac MLCK protein, the mutation of which is associated with hereditary increased susceptibility to cardiac dysfunction. A mutation of the cardiac MLCK gene can include nucleotide sequence changes, additions or deletions, including deletion of large portions or the entire cardiac MLCK gene, or duplications of all or substantially all of the gene. Alternatively, genetic expression of cardiac MLCK can be deregulated such that cardiac MLCK is over or under expressed. The term "cardiac MLCK gene" is understood to include the various sequence polymorphisms and allelic variations that exist within the population. This term relates primarily to an isolated coding sequence, but can also include some or all of the flanking regulatory elements and/or intron sequences.

Mutant forms and altered expression of the cardiac MLCK gene can be associated with hereditary cardiomyopathy. The RNA transcribed from a mutant cardiac MLCK gene is mutant cardiac MLCK messenger RNA.

Cardiac MLCK cDNA: A cDNA molecule which, when transfected or otherwise introduced into cells, expresses the cardiac MLCK protein. The cardiac MLCK cDNA can be derived, for instance, by reverse transcription from the mRNA encoded by the cardiac MLCK gene and lacks internal non-coding segments and transcription regulatory sequences present in the cardiac MLCK gene. The prototypical human cardiac MLCK cDNA is shown in SEQ ID NO: 1.

Cardiac dysfunction: any impairment in the heart's pumping function. This includes, for example, impairments in contractility, impairments in ability to relax (sometimes referred to as diastolic dysfunction), abnormal or improper functioning of the heart's valves, diseases of the heart muscle (sometimes referred to as cardiomyopathy), diseases such as angina and myocardial infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart (for example, atrial septal defect). For further discussion, see Braunwald, Heart Disease: a Textbook of Cardiovascular Medicine, 5th edition 1997, WB Saunders Company, Philadelphia Pa. (hereinafter Braunwald).

Cardiomyopathy: any disease or dysfunction of the myocardium (heart muscle). These can be inflammatory, metabolic, toxic, infiltrative, fibroplastic, hematological, genetic, or unknown in origin. They are generally classified into three groups based primarily on clinical and pathological characteristics:

(1) dilated cardiomyopathy, a syndrome characterized by cardiac enlargement and impaired systolic function of one or both ventricles;

(2) hypertrophic cardiomyopathy, herein defined as (a) global or regional increase in thickness of either ventricular wall or the interventricular septum, or (b) an increased susceptibility to global or regional increase in thickness of either ventricular wall or the interventricular septum, such as can occur in genetic diseases, hypertension, or heart valve dysfunction; or (3) restrictive and infiltrative cardiomyopathies, a group of diseases in which the predominate clinical feature is usually impaired ability of the heart to relax (diastolic dysfunction), and often characterized by infiltration of the heart muscle with foreign substances such as amyloid fibers, iron, or glycolipids.

See Wynne and Braunwald, The Cardiomyopathies and Myocarditities, Chapter 41 in Braunwald.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

DNA: deoxyribonucleic acid. DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Deletion: The removal of a sequence of DNA, the regions on either side being joined together.

Effective amount of a compound: A quantity of compound sufficient to achieve a desired effect in a subject being treated. For instance, this can be the amount necessary to increase the heart rate or cardiac contractility of the subject. In general, this amount will be sufficient to measurably increase the number of beats per minute of the heart, or sufficient to increase cardiac contractility in some measurable way, such as by echocardiography, measurement of cardiac output, or improvement in signs or symptoms of congestive heart failure.

An effective amount of a compound can be administered in a single dose, or in several doses, for example daily, during a course of treatment However, the effective amount of the compound will be dependent on the compound applied, the subject being treated, the severity and type of the affliction, and the manner of administration of the compound.

The general term "administering to the subject" is understood to include all animals (e.g. humans, apes, dogs, cats, horses, and cows) that have or may develop some form of cardiac dysfunction.

Electrical pacing: controlling or attempting to control the rate at which the heart beats by external electrical stimulation. See Barold et al., *Cardiac Pacemakers and Antiarrythmic Devices,* Chapter 23 in Braunwald for a more detailed discussion.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Functional fragments and variants of a polypeptide: includes those fragments and variants that maintain one or more functions of the parent polypeptide. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential functions of a protein. See Stryer, Biochemistry 3rd Ed., (c) 1988. Third, part of a polypeptide chain can be deleted without impairing or eliminating all of its functions. Fourth, insertions or additions can be made in the polypeptide chain—for example, adding epitope tags—without impairing or eliminating its functions (Ausubel et al., 1997). Other modifications that can be made without materially impairing one or more functions of a polypeptide include, for example, in vivo or in vitro chemical and biochemical modifications or which incorporate unusual amino acids. Such modifications include, for example, acetylation, carboxylation, phosphorylation, glycosylation, ubiquination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$P, ligands which bind to labeled antiligands (e.g., antibodies), fluorophores, chemiluminescent agents, enzymes, and antiligands. Functional fragments and variants can be of varying length. For example, some fragments have at least 10, 25, 50, 75, 100, or 200 amino acid residues.

A functional fragment or variant of myosin light chain is defined herein as a polypeptide which is capable of being phosphorylated by a protein having myosin light chain kinase biological activity. It includes any polypeptide six or more amino acid residues in length which is capable of being phosphorylated by a protein having myosin light chain kinase biological activity.

Heart: the muscular organ of an animal that circulates blood.

In mammals, the heart is comprised of four chambers: right atrium, right ventricle, left atrium, left ventricle. The right atrium and left atrium are separated from each other by an interatrial septum, and the right ventricle and left ventricle are separated from each other by an interventricular septum. The right atrium and right ventricle are separated from each other by the tricuspid valve. The left atrium and left ventricle are separated from each other by the mitral valve.

The walls of the heart's four chambers are comprised of working muscle, or myocardium, and connective tissue. Myocardium is comprised of myocardial cells, which are also referred to herein as cardiac cells, cardiac myocytes, cardiomyocytes and/or cardiac fibers. Myocardial cells can be isolated from a subject and grown in vitro. The inner layer of myocardium closest to the cavity is termed endocardium, and the outer layer of myocardium is termed epicardium. The left ventricular cavity is bounded in part by the interventricular septum and the left ventricular free wall. The left ventricular free wall is sometimes divided into regions, such as anterior wall, posterior wall and lateral wall; or apex (the tip of the left ventricle, furthest from the atria) and base (part of the left ventricle closest to the atria). Apical and basal are adjectives that refer to the corresponding region of the heart.

In operation, the heart's primary role is to pump sufficient oxygenated blood to meet the metabolic needs of the tissues and cells in a subject. The heart accomplishes this task in a rhythmic and highly coordinated cycle of contraction and relaxation referred to as the cardiac cycle. For simplicity, the cardiac cycle may be divided into two broad categories: ventricular systole, the phase of the cardiac cycle where the ventricles contract; and ventricular diastole, the phase of the cardiac cycle where the ventricles relax. See Opie, Chapter 12 in Braunwald for a detailed discussion. Used herein, the terms systole and diastole are intended to refer to ventricular systole and diastole, unless the context clearly dictates otherwise.

In normal circulation during health, the right atrium receives substantially deoxygenated blood from the body via the veins. In diastole, the right atrium contracts and blood flows into the right ventricle through the tricuspid valve. The right ventricle fills with blood, and then contracts (systole). The force of systole closes the tricuspid valve and forces blood through the pulmonic valve into the pulmonary artery. The blood then goes to the lungs, where it releases carbon dioxide and takes up oxygen. The oxygenated blood returns to the heart via pulmonary veins, and enters the left atrium. In diastole, the left atrium contracts and blood flows into the left ventricle through the mitral valve. The left ventricle fills with blood and then contracts, substantially simultaneously with right ventricular contraction. The force of contraction closes the mitral valve and forces blood through the aortic valve into the aorta. From the aorta, oxygenated blood circulates to all tissues of the body where it delivers oxygen to the cells. Deoxygenated blood then returns via the veins to the right atrium.

In the cavity of left ventricle, there are two large, essentially cone-shaped extensions of the ventricular myocardium known as the anterior and posterior papillary muscles. These connect to the ventricular surface of the mitral valve via threadlike extensions termed chordae tendiniae or chordae. One important role for the papillary muscles and chordae is to ensure that the mitral valve stays closed during ventricular systole. Another important role is to add to the force of cardiac contraction. Similarly, the right ventricle has papillary muscles and chordae which tether the tricuspid valve and add to the force of contraction.

Due to inherited or acquired disease processes and/or normal aging, the heart muscle can develop dysfunction of either systole or diastole, or both. Dysfunction of systole is referred to as systolic dysfunction. Dysfunction of diastole is referred to as diastolic dysfunction. See Opie Chapter 12, and Colucci et al., Chapter 13 in Braunwald for a detailed discussion.

Due to inherited or acquired disease processes and/or normal aging, one or more of the heart valves may develop dysfunction. Valvular dysfunction generally falls into two broad categories: stenosis, defined herein as incomplete opening of the valve during a time of the cardiac cycle when a normally operating valve is substantially open; and insufficiency, defined herein as incomplete closing of the valve during a time of the cardiac cycle when a normally operating valve is substantially closed. Valvular dysfunction also includes a condition known as mitral valve prolapse, wherein the mitral valve leaflets prolapse backward into the left atrium during ventricular systole. The condition may be associated with mild, moderate, or severe insufficiency of the mitral valve.

Valvular stenosis is typically characterized by a pressure gradient across the valve when the valve is open. Valvular insufficiency is typically characterized by retrograde ("backward") flow when the valve is closed. For example, mitral stenosis is characterized by a pressure gradient across the mitral valve near the end of ventricular diastole (as a typical example of moderate mitral stenosis, 5 mm Hg diastolic pressure in the left ventricle, 20 mm Hg diastolic pressure in the left atrium, for a pressure gradient of 15 mm Hg). As another example, mitral insufficiency is characterized by "backward" flow of blood from the left ventricle into the left atrium during ventricular systole.

Heart failure: the inability of the heart to supply sufficient oxygenated blood to meet the metabolic needs of the tissues and cells in a subject. This can be accompanied by circulatory congestion, such as congestion in the pulmonary or systemic veins. As used herein, the term heart failure encompasses heart failure from any cause, and is intended herein to encompass terms such as "congestive heart failure," "forward heart failure," "backward heart failure," "high output heart failure," "low output heart failure," and the like. See Chapters 13-17 in Braunwald for a detailed discussion.

Isolated: An "isolated" biological component (such as a nucleic acid molecule, protein or organelle) has been substantially separated or purified away from other biological components in the cell of the organism in which the component naturally occurs, i.e., other chromosomal and extrachromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Labeled: a biomolecule attached covalently or noncovalently to a detectable label or reporter molecule. Typical labels include radioactive isotopes, enzyme substrates, cofactors, ligands, chemiluminescent or fluorescent agents, haptens, and enzymes. Methods for labeling and guidance in the choice of labels appropriate for various purposes are discussed, e.g., in Sambrook et al., *Molecular Cloning: A Laboratory Manual*, CSHL, New York, 1989 and Ausubel et al., *Current Protocols in Molecular Biology*, Greene Publ. Assoc. and Wiley-Intersciences, 1998. For example, ATP can be labeled in any one of its three phosphate groups with radioisotopes such as $^{32}$P or $^{33}$P, or in its sugar moiety with a radioisotopes such as $^{35}$S.

Myosin light chain: an approximately 18 kDa protein which associates with the myosin heavy chain and participates in the regulation of myosin's force-generating ATPase activity. There are two major groupings of MLC: MLC1, sometimes referred to as the essential myosin light chain, abbreviated ELC; and MLC2, sometimes referred to as the regulatory myosin light chain, abbreviated RLC. RLC is the primary biological target of MLCK-mediated phosphorylation. When phosphorylated by MLCK the phosphorylated form of RLC is abbreviated RLC-P. Isoforms of ELC and RLC existing in skeletal, smooth, and cardiac muscle have been described. As an example, the human cardiac RLC gene and cDNA are described by Macera et al., Genomics 13: 829-31, 1992 (GenBank accession no. NM00432).

Myosin light chain kinase biological activity: the in vitro or in vivo enzymatic ability of a polypeptide or protein to mediate covalent incorporation of a phosphate into a regulatory myosin light chain. The term encompasses such enzymatic activity observed with any isoform of MLCK (for example, nonmuscle, smooth muscle, skeletal muscle, and cardiac MLCK isoforms), as well as such enzymatic activity observed with fragments and variants of MLCK isoforms (for example, naturally occurring mutants; mutations, insertions and deletions introduced through recombinant DNA techniques; and fragments of MLCK generated by proteolysis).

Muscle cell: include skeletal, cardiac or smooth muscle tissue cells. This term is synonymous with myocyte, and encompasses those cells which differentiate to form more specialized muscle cells (e.g. myoblasts). "Cardiomyocyte" refers to a cardiac muscle cell, or cells that differentiate to form cardiomyocytes.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Probes and primers: Nucleic acid probes and primers can be readily prepared based on the nucleic acid molecules provided in this invention. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g. in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides 10 nucleotides or more in length. More preferably, longer DNA oligonucleotides can be about 15, 17, 20, or 23 nucleotides or more in length Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of the cardiac MLCK encoding nucleotide will anneal to a target sequence, such as another cardiac MLCK gene homolog from the gene family contained within a human genomic DNA library, with a higher specificity than a corresponding primer of only 15 nucleotides. Thus, in order to obtain greater specificity, probes and primers can be selected that comprise at least 17, 20, 23, 25, 30, 35, 40, 45, 50 or more consecutive nucleotides of cardiac MLCK nucleotide sequences.

The invention thus includes isolated nucleic acid molecules that comprise specified lengths of the disclosed cardiac MLCK cDNA sequences. Such molecules can comprise at least 17, 20, 23, 25, 30, 35, 40, 45 or 50 consecutive nucleotides of these sequences, and can be obtained from any region of the disclosed sequences. By way of example, the cardiac MLCK cDNA sequences can be apportioned into halves or quarters based on sequence length, and the isolated nucleic acid molecules can be derived from the first or second halves of the molecules, or any of the four quarters. By way of example, the human cardiac MLCK cDNA, ORF, coding sequence and gene sequences can be apportioned into about halves or quarters based on sequence length, and the isolated nucleic acid molecules (e.g., oligonucleotides) can be derived from the first or second halves of the molecules, or any of the four quarters. The human cardiac MLCK cDNA (SEQ ID NO: 1) can be used to illustrate this. The human cardiac MLCK cDNA is 18207 nucleotides in length and so can be hypothetically divided into about halves (nucleotides 1-9103 and 9104-18207) or about quarters (nucleotides 1-4551, 4552-9103, 9104-13464 and 13465-18207). The cDNA also could be divided into smaller regions, e.g. about eighths, sixteenths, twentieths, fiftieths and so forth, with similar effect.

Alternatively, the coding sequence of the human cardiac MLCK cDNA can be thus apportioned into about halves or quarters, and oligonucleotides derived from any such portion. The coding sequence of cardiac MLCK is 16190 nucleotides in length, and corresponds to nucleotides 230-17140 of the cDNA (SEQ ID NO: 1). The coding sequence thus can be hypothetically divided into about halves (nucleotides 1-8455 and 8456-16910 of the coding sequence, corresponding to positions 230-8685 and 8686-17140, respectively, of SEQ ID NO: 1) or about quarters (nucleotides 1-4227, 4228-8455, 8465-12683 and 12683-16190 of the coding sequence, corresponding to positions 230-4457, 4458-8685, 8686-12913, and 12914-17140, respectively, of SEQ ID NO: 1). The coding sequence of cardiac MLCK also could be divided into smaller regions, e.g. about eighths, sixteenths, twentieths, fiftieths and so forth, with similar effect.

Protein: A biological molecule expressed by a gene and comprised of amino acids.

Purified: The term "purified" does not require absolute purity; rather, it is intended as a relative term. Thus, for example, a purified protein preparation is one in which the protein referred to is more pure than the protein in its natural environment within a cell.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of the cardiac MLCK protein, and the corresponding cDNA sequence, will possess a relatively high degree of sequence identity when aligned using standard methods. This homology will be more significant when the orthologous proteins or cDNAs are derived from species which are more closely related (e.g., human and chimpanzee sequences), compared to species more distantly related (e.g., human and C. elegans sequences).

Typically, cardiac MLCK orthologs are at least 50% identical at the nucleotide level and at least 50% identical at the amino acid level when comparing human cardiac MLCK to an orthologous cardiac MLCK.

Methods of alignment of sequences for comparison are well known in the art. Various programs and alignment algorithms are described in: Smith & Waterman (1981) *Adv. Appl. Math.* 2: 482; Needleman & Wunsch (1970) *J. Mol. Biol.* 48: 443; Pearson & Lipman (1988) *Proc. Natl. Acad. Sci. USA* 85: 2444; Higgins & Sharp (1988) *Gene,* 73: 237-244; Higgins & Sharp (1989) *CABIOS* 5: 151-153; Corpet et al. (1988) *Nuc. Acids Res.* 16, 10881-90; Huang et al. (1992) *Computer Appls. in the Biosciences* 8, 155-65; and Pearson et al. (1994) *Meth. Mol. Bio.* 24, 307-31. Altschul et al. (1990) *J. Mol. Biol.* 215:403-410, presents a detailed consideration of sequence alignment methods and homology calculations.

The NCBI Basic Local Alignment Search Tool (BLAST) (Altschul et al. (1990) *J. Mol. Biol.* 215:403-410) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity using this program.

Homologs of the disclosed human cardiac MLCK protein typically possess at least 60% sequence identity counted over full-length alignment with the amino acid sequence of human cardiac MLCK using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30-amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described in the NCBI website.

These sequence identity ranges are provided for guidance only, it is entirely possible that strongly significant homologs could be obtained that fall outside of the ranges provided. The present invention provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (1989) *Molecular Cloning: A Laboratory Manual*, CSHL, New York and Tijssen (1993) *Laboratory Techniques in Biochemistry and Molecular Biology—Hybridization with Nucleic Acid Probes* Part I, Chapter 2, Elsevier, N.Y. Nucleic acid molecules that hybridize under stringent conditions to a human cardiac MLCK gene sequence will typically hybridize to a probe based on either an entire human cardiac MLCK gene or selected portions of the gene under wash conditions of 2×SSC at 50° C. A more detailed discussion of hybridization conditions is presented below.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: An agent that binds substantially only to a defined target Thus a cardiac MLCK protein-specific binding agent binds substantially only the cardiac MLCK protein. As used herein, the term "cardiac MLCK protein specific binding agent" includes anti-cardiac MLCK protein antibodies and other agents (such as soluble receptors) that bind substantially only to the cardiac MLCK protein.

Anti-cardiac MLCK protein antibodies can be produced using standard procedures described in a number of texts, including Harlow and Lane (*Antibodies, A Laboratory Manual*, CSHL, New York, 1988). The determination that a particular agent binds substantially only to the cardiac MLCK protein can readily be made by using or adapting routine procedures. One suitable in vitro assay makes use of the Western blotting procedure (described in many standard texts, including Harlow and Lane, *Antibodies, A Laboratory Manual*, CSHL, New York, 1988). Western blotting can be used to determine that a given cardiac MLCK protein binding agent, such as an anti-cardiac MLCK protein monoclonal antibody, binds substantially only to the cardiac MLCK protein.

A phosphospecific binding agent specifically binds to a peptide containing a phosphorylated residue.

Shorter fragments of antibodies can also serve as specific binding agents. For instance, Fabs, Fvs, and single-chain Fvs (SCFvs) that bind to cardiac MLCK would be cardiac MLCK-specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The object of identifying the hitherto unknown cMLCK gene has been achieved by providing an isolated human cDNA molecule and genomic DNA structure. Specifically, the disclosure provides, for the first time, an isolated cDNA molecule which, when transfected into cells can produce the cMLCK protein linked to cardiac dysfunction, cardiac hypertrophy and certain forms of cardiomyopathy such as hypertrophic cardiomyopathy and mid-cavitary ventricular hypertrophy. The disclosure encompasses the cMLCK cDNA molecule, the nucleotide sequence of this cDNA, and the putative amino acid sequence of the cMLCK protein encoded by this cDNA.

Having herein provided the nucleotide sequence of the cMLCK cDNA, correspondingly provided are the complementary DNA strands of the cDNA molecule and DNA molecules which hybridize under stringent conditions to the cMLCK cDNA molecule or its complementary strand. Such hybridizing molecules include DNA molecules differing only by minor sequence changes, including nucleotide substitutions, deletions and additions. Also comprehended by this invention are isolated oligonucleotides comprising at least a segment of the cDNA molecule or its complementary strand, such as oligonucleotides, which can be employed as effective DNA hybridization probes or primers useful in the polymerase chain reaction. Such probes and primers are particularly useful in the screening and diagnosis of persons genetically predisposed to hypertrophic cardiomyopathy and other forms of cardiac dysfunction, as the result of cMLCK gene mutations. Generally, these oligonucleotides will be 10 contiguous nucleotides long or longer, and preferably 20 contiguous nucleotides long or longer, and can be at least 25, 30, 35, 40, 45, or 50 contiguous nucleotides in length.

Recombinant DNA vectors comprising the disclosed DNA molecules, and transgenic host cells containing such recombinant vectors, are also provided. Disclosed embodiments include transgenic nonhuman animals which over- or under-express the cMLCK protein, or over- or under-express fragments or variants of cMLCK protein.

A disclosed embodiment is a method for screening a subject to determine if the subject carries a mutant cMLCK gene, or if the gene has been partially or completely deleted or duplicated. The method includes the steps of: providing a biological sample obtained from the subject, which sample includes DNA or RNA, and providing an assay for detecting in the biological sample the presence of a mutant cMLCK gene, a mutant cMLCK RNA, or the absence, through partial or complete deletion, of the cMLCK gene and corresponding RNA, or the presence of multiple copies of the cMLCK encoding region through duplication.

The foregoing assay can be assembled in the form of a diagnostic kit and in some embodiments includes: hybridization with oligonucleotides; PCR amplification of the cMLCK gene or a part thereof using oligonucleotide primers; RT-PCR amplification of the cMLCK RNA or a part thereof using oligonucleotide primers; or direct sequencing of the cMLCK gene of the subject's genome using oligonucleotide primers. The efficiency of these molecular genetic methods permits a rapid classification of patients affected by deletions or mutations of the cMLCK gene.

A further aspect of the present disclosure is a method for screening a subject to assay for the presence of a mutant, or partially or entirely duplicated or deleted cMLCK gene, by providing a biological sample of the subject which sample contains cellular proteins, and providing an immunoassay for quantitating the level of cMLCK protein in the biological sample, or a level of activity of the protein. Diagnostic methods for the detection of mutant, duplicated or deleted cMLCK genes made possible by this invention, or the detection of abnormal protein function or expression, provides an enhanced ability to diagnose susceptibility to hereditary cardiac dysfunction.

Another aspect of the disclosure is a preparation comprising one or more binding agents that specifically detect the cMLCK protein. Such specific binding agents can be antibodies, for insane monoclonal antibodies or polyclonal antibodies. In addition, the invention provides specific binding agents for the human regulatory myosin light chain in its MLCK-phosphorylated form.

Also disclosed is a method for detecting enhanced susceptibility of a subject to cardiac dysfunction, by detecting decreased, increased, or mutant cMLCK in the subject's cells, such as cardiac or muscle cells. Enhanced susceptibility to dysfunction can also be detected by transforming a cell with cDNA encoding cMLCK from the subject, expressing the cMLCK, and evaluating its myosin light chain kinase biological activity.

The disclosure also provides methods for enhancing or preserving the cardiac function of a subject, by modulating the subject's cardiac stretch activation, for example, by modulating myosin phosphorylation or the cMLCK biological activity in the myocardial cells of the subject. Disclosed methods for modulating cMLCK biological activity include, for example, administering to the subject an effective amount of a compound that modulates cMLCK activity, or delivering to the subject's heart a vector encoding a peptide that modulates cMLCK activity. The vector can be delivered, for example, to specific regions of the heart, such as papillary muscle or left ventricular free wall. The methods can be used to treat cardiac dysfunction, for example, systolic dysfunction, diastolic dysfunction, cardiac hypertrophy, cardiomyopathy, coronary heart disease, myocardial infarction, and congestive heart failure.

Methods are further provided for screening for agents which can modulate cMLCK biological activity, by incubating a putative modulator agent with a protein having cMLCK biological activity and a polypeptide which can serve as a substrate for that protein, and detecting phosphorylation of the polypeptide. Two or more concentrations of the putative modulatory agent can be compared for their ability to modulate cMLCK activity, by comparing an extent of polypeptide phosphorylation at the two concentrations. Alternatively, two or more different putative modulatory agents can also be compared. Phosphorylation of the peptide can be detected with a specific binding agent which specifically binds the phosphorylated form of the polypeptide, or by detecting incorporation of labeled phosphate into the polypeptide. A secondary specific binding agent, which can be labeled, can be used to detect the specifically bound primary specific binding agent.

II. cMLCK Protein and Nucleic Acid Sequences

This invention provides cMLCK proteins and cMLCK nucleic acid molecules, including cDNA sequences. The prototypical cMLCK sequences are the human sequences, and the invention provides for the use of these sequences to produce transgenic animals having increased or decreased levels of cMLCK protein, as well as diagnostic methods to detect defects or alterations in cMLCK expression or cMLCK protein production. Also provided is the human cMLCK genomic structure and sequence.

The full-length cDNA for cMLCK is 1791 base pairs long, and encodes a protein of 596 amino acids (SEQ ID NO:1 and SEQ ID NO:2).

Cloning and Sequence Determination of the cMLCK cDNA and Genomic DNA from Rabbit Heart Since the first report that cardiac myosin RLC is phosphorylated in vivo, there has been an unsuccessful search for the responsible kinase. Because slow skeletal muscle myosin and its RLC are the primary cardiac ventricular isoforms in many animals, the skeletal MLCK was considered to be the likely responsible kinase in heart. However, attempts to demonstrate skeletal MLCK in the heart have been unsuccessful.

Published rabbit skeletal muscle MLCK cDNA sequence was used to design a set of primer pairs to amplify unique fragments from both rabbit skeletal muscle and cardiac RNA. A product from one pair of primers (upstream 5'-TGATCCAGCTGTACGCAGCC-3" (SEQ ID NO: 19), downstream 5'-CTTGAGGTCCAGGTGCAGC-3' (SEQ. ID NO:20)) yielded identically sized 201 bp fragments from both templates. Subcloning and sequencing showed identical sequences suggesting that either skeletal muscle MLCK or a partially homologous isoform could be found in rabbit cardiac muscle. A possible genomic contamination was excluded since the same primers crossed an intron-exon boundary and generated a greater than 500 bp size fragment from rabbit genomic DNA. The divergence of the latter genomic sequence from the cDNA sequence marked what was later found to be the homologue of the human intron-exon-6 boundary.

Cloning and Sequence Determination of the Human cMLCK cDNA and Genomic DNA

Next, human genomic DNA was used as a template from which a MLCK fragment was amplified using primers derived from the rabbit sequence. In order to avoid cross-reaction with human smooth muscle MLCK sequence, the DNA sequence flanking the homologous intron-6 insertion point of rabbit skeletal and smooth muscle MLCK was compared. A downstream region of amino acid divergence was identified in the presumed region of skeletal MLCK exon 7. The nucleotide sequence encoding this stretch was then compared for differences between rabbit and rat skeletal muscle MLCK cDNA sequence. A degenerate primer was prepared that encoded both rat and rabbit sequence as well as some possible $3^{rd}$ position codon changes. (5'-AGGTCCAg/aGTGCAGc/a/t/gACCCg/tCA-3' (SEQ ID NO: 21)) Upstream primers in presumed human exon 6 that were divergent between rabbit smooth and skeletal muscle MLCK were conserved between rat and rabbit skeletal MLCK sequence. Thus, minimal changes from the rabbit upstream primer sequence were made (5'-CGTg/cCTGT-TCATGGAGT-3' (SEQ ID NO: 22)). Using the latter 2 primers, the fragment obtained from human genomic DNA contained an 82 bp intron. Subcloning and sequencing yielded coding sequence, which internal to the primer ends, showed significant homology at the amino acid level to rabbit skeletal muscle MLCK.

In order to obtain a full length clone from human cardiac RNA, 5' and 3' RACE was performed using the Marathon RACE kit (Clontech). The exon 6 sequence obtained from human DNA was used to generate 2 primers for 5' and 3' RACE. The 5' RACE fragment was denatured and annealed to the human exon 6 containing fragment. PCR amplification using primers from the 5' ends of both fragments were used to join both fragments. A similar process was then used to join this fragment with the 3' RACE product to produce a full length cDNA fragment. This full length cDNA was sequenced and matched the sequence of the RT-PCR amplified product from human skeletal muscle.

In order to obtain full length genomic sequence, a primer based in human intron 6 (5'-CCACGGCTTrGCTCCGT-GCCT-3' (SEQ ID NO: 23)) was used together with an upstream exon 6 primer (5'-ATCGAGACTCCGCAT-GAGAT-3' (SEQ ID NO: 24)) to screen a human P1 library (Genome Systems). Intron-exon boundaries were established by amplifying the intervening introns using cDNA sequence derived primers as well as direct sequencing of the P1 clone. Sequence of the coding portions of the genomic clone matched the full length cDNA sequence obtained through RACE. There was significant homology between the predicted amino acid translation of the human cMLCK sequence and rabbit skeletal muscle MLCK sequence. However, amino acid sequence divergence was substantial in the amino-terminal end.

The genomic DNA of human cMLCK comprises 12 exons.

The following examples help illustrate the specific applications of this technology.

EXAMPLE 1

Method of Making cMLCK Encoding Sequences

The foregoing discussion describes the original means by which the cMLCK cDNAs were obtained and also provides the nucleotide sequence of these clones. It also describes the genomic structure and sequence of rabbit and human cMLCK. With the provision of this sequence information, the polymerase chain reaction (PCR) or other similar amplification techniques can be used in a more direct and simple method for producing cMLCK encoding sequences.

Total RNA is extracted from human cells by any one of a variety of methods well known to those of ordinary skill in the art. Sambrook et al. (In *Molecular Cloning: A Laboratory Manual*, CSHL, New York, 1989) and Ausubel et al. (In *Current Protocols in Molecular Biology*, John Wiley & Sons, New York, 1998) provide descriptions of methods for RNA isolation. In one embodiment, human myocardial cells obtained from a myocardial biopsy, or cultured human myocytes from a non-cMLCK deleted individual are utilized. The extracted RNA is then used as a template for performing the reverse transcription-polymerase chain reaction (RT-PCR) amplification of cDNA. Methods and conditions for RT-PCR are described in Kawasaki et al., In *PCR Protocols, A Guide to Methods and Applications*, Innis et al. (eds.), 21-27, Academic Press, Inc., San Diego, Calif., 1990. The selection of PCR primers is made according to the portions of the cDNA which are to be amplified. Primers are chosen to amplify small segments of a cDNA or the entire cDNA molecule. Variations in amplification conditions are required to accommodate primers and amplicons of differing lengths and composition; such considerations are well known in the art and are discussed in innis et al. (*PCR Protocols, A Guide to Methods and Applications*, Academic Press, Inc., San Diego, Calif., 1990). cMLCK encoding sequences can be amplified theoretically using the following combination of primers:

```
primer 1
5' atg gcg aca gaa aat gg 3'      (SEQ ID NO: 17)

primer 3
5' tca gac ccc cag agc ca 3'.     (SEQ ID NO: 18)
```

These primers are illustrative only; one skilled in the art will appreciate that many different primers can be derived from the provided cDNA sequence in order to amplify particular regions of these cDNAs.

Re-sequencing of PCR products obtained by these amplification procedures is performed; this facilitates confirmation of the amplified sequence and also provides information on natural variation on this sequence in different populations or species. Oligonucleotides derived from the provided cMLCK sequences provided are used in such sequencing methods.

Orthologs of human cMLCK are cloned in a similar manner, where the starting material consists of myocytes or cardiomyocytes taken from a non-human species. Orthologs will generally share at least 50% sequence homology with the disclosed human cMLCK cDNA. Where the non-human species is more closely related to humans, the sequence homology is generally greater. Closely related orthologous cMLCK molecules can share at least 75%, at least 80%, at least 90%, at least 95%, or at least 98% sequence homology with the disclosed human sequences.

Oligonucleotides derived from the human cMLCK cDNA sequence (SEQ ID NO: 1), are encompassed within the scope of the present invention. Such oligonucleotide primers can for example include a sequence of at least 10 consecutive nucleotides of the cMLCK nucleic acid sequence. To enhance amplification specificity, oligonucleotide primers comprising at least 15, 25, 30, 35, 40, 45 or 50 or more consecutive nucleotides of these sequences can also be used. These primers for instance can be obtained from any region of the disclosed sequences. By way of example, the human cMLCK cDNA, ORF and gene sequences may be apportioned into about halves or quarters based on sequence length, and the isolated nucleic acid molecules (e.g., oligonucleotides) are derived from the first or second halves of the molecules, or any of the four quarters. The human cMLCK cDNA, shown in SEQ ID NO: 1, can be used to illustrate this. The portion of the prototypical human cMLCK cDNA shown in SEQ ID NO: 1 is 1791 nucleotides in length and so can be hypothetically divided into about halves (nucleotides 1-895 and 896-1791) or about quarters (nucleotides 1-448, 449-895, 896-1343 and 1344-1791).

In one embodiment, nucleic acid molecules are selected that comprise at least 10, 15, 20, 25, 30, 35, 40, 50 or 100 or more consecutive nucleotides of any of these or other portions of the human cMLCK cDNA, or of the 5' or 3' flanking regions. Thus, representative nucleic acid molecules might include at least 10 consecutive nucleotides of the region comprising nucleotides 1-448, 449-895, 896-1343 and 1344-1791 of the disclosed human cMLCK coding sequence.

EXAMPLE 2

Cloning of the CMLCK Genomic Gene

Some mutations in the cMLCK gene can lead to development or progression of cardiac dysfunction (e.g., cardiomyopathy) are not included in the cDNA but rather are located in other regions of the cMLCK gene. Mutations located outside of the open reading frame that encodes the cMLCK protein are not likely to affect the functional activity of the protein but rather are likely to result in altered levels of the protein in the cell. In one embodiment, a mutation in the promoter region of the cMLCK gene prevents transcription of the gene and therefore leads to the complete absence of the cMLCK protein in the cell. Alternatively, a mutation in the promoter region leads to unregulated or mis-regulated expression of cMLCK, including for instance overexpression or mislocalized or mis-timed expression.

Additionally, mutations within intron sequences in the genomic gene can also prevent expression of the cMLCK protein. Following transcription of a gene containing introns, the intron sequences are removed from the RNA molecule in a process termed splicing prior to translation of the RNA molecule which results in production of the encoded protein. When the RNA molecule is spliced to remove the introns, the cellular enzymes that perform the splicing function recognize sequences around the intron/exon border and in this manner recognize the appropriate splice sites. If there is a mutation within the sequence of the intron close to the junction of the intron with an exon, the enzymes may not recognize the junction and can thus fail to remove the intron. If this occurs, the encoded protein can be defective. Thus, mutations inside the intron sequences within the cMLCK gene (termed "splice site mutations") can also lead to the development or progression of cardiac dysfunction. However, knowledge of the exon structure and intronic splice site sequences of the cMLCK gene is required to define the molecular basis of these abnormalities. The provision herein of the cMLCK genomic structure and intron-exon boundaries (see Example 17) enables diagnosis of a genetic predisposition to cardiac dysfunction and cardiomyopathy based on DNA analysis, and allows an analysis of all possible mutagenic events at the cMLCK locus.

With the sequences of the cMLCK cDNA and cMLCK gene in hand, primers derived from these sequences can be used in diagnostic tests (described below) to determine the presence of mutations (including genomic amplifications or deletions) in any part of the genomic cMLCK gene of a subject, as well as 3' and 5' flanking sequences. Such primers can be, for example oligonucleotides including a fragment of sequence from the cMLCK gene (intron sequence, exon sequence or a sequence spanning an intron-exon boundary, or flanking region) and can include, for example, at least 10 consecutive nucleotides of the cMLCK cDNA or gene. It will be appreciated that greater specificity can be achieved by using primers of greater lengths. Thus, in order to obtain enhanced specificity, the primers used can comprise at least 10, 15, 17, 20, 23, 25, 30, 40 or even 50 or 100 or more consecutive nucleotides of the cMLCK cDNA, gene or flanking region. Furthermore, with the provision of the cMLCK intron sequence information the analysis of a large and as yet untapped source of patient material for mutations will now be possible using methods such as chemical cleavage of mismatches (Cotton et al., *Proc. Natl. Acad. Sci. USA* 85:4397-4401, 1985; Montandon et al., *Nucleic Acids Res.* 9:3347-3358, 1989) and single-strand conformational polymorphism analysis (Orita et al., *Genomics* 5:874-879, 1989).

Additional experiments can be performed to identify and characterize regulatory elements flanking the cMLCK gene. These regulatory elements can be characterized by standard techniques including deletion analyses wherein successive nucleotides of a putative regulatory region are removed and the effect of the deletions are studied by either transient or long-term expression analyses experiments. The identification and characterization of regulatory elements flanking the genomic cMLCK gene can be made by functional experimentation (deletion analyses, etc.) in mammalian cells by either transient or long-term expression analyses.

Either the genomic clone or the cDNA or sequences derived from these clones can be used in applications of this invention, including but not limited to, studies of the expression of the cMLCK gene, studies of the function of the cMLCK protein, the generation of antibodies to the cMLCK protein diagnosis and therapy of cMLCK amplified, deleted or mutated patients to prevent or treat the onset or progression of cardiac dysfunction or cardiomyopathy. Descriptions of applications of the use of cMLCK cDNA are therefore intended to comprehend the use of the genomic cMLCK gene. It will also be apparent to one skilled in the art that homologs of this gene can now be cloned from other species, such as the rat, by standard cloning methods. Such homologs are useful in the production of animal models of cardiac dysfunction onset and disease progression. In general, such orthologous cMLCK molecules will share at least 50% sequence identity with the human cMLCK nucleic acid disclosed herein; more closely related orthologous sequences will share at least 60%, at least 75%, at least 80%, at least 90%, at least 95%, or at least 98% sequence identity with this sequence.

EXAMPLE 3

Nucleotide and Amino Acid Sequence Variants of cMLCK

With the provision of human cMLCK protein and corresponding nucleic acid sequences herein, the creation of variants of these sequences is now enabled.

Variant cMLCK proteins include proteins that differ in amino acid sequence from the human cMLCK sequences disclosed but that share at least 50% amino acid sequence homology with the provided human cMLCK protein. Other variants will share at least 60%, at least 75%, at least 80%, at least 90%, at least 95%, or at least 98% amino acid sequence homology. Manipulation of the nucleotide sequence of cMLCK using standard procedures, including for instance site-directed mutagenesis or PCR, can be used to produce such variants. The simplest modifications involve the substitution of one or more amino acids for amino acids having similar biochemical properties. These "conservative substitutions" are likely to have minimal impact on the activity of the resultant protein. Table 2 shows amino acids that may be substituted for an original amino acid in a protein, and which are regarded as conservative substitutions.

TABLE 2

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |

TABLE 2-continued

| Original Residue | Conservative Substitutions |
|---|---|
| Trp | tyr |
| Tyr | trp; phe |
| Val | ile; leu |

More substantial changes in enzymatic function or other protein features may be obtained by selecting amino acid substitutions that are less conservative than those listed in Table 2. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g. leucyl, isoleucyl, phenylalanyl, valyl or alanyl); (b) a cysteine or proline is substituted for (or by) any other residue; (c) a residue having an electropositive side chain (e.g. lysyl, arginyl, or histadyl) is substituted for (or by) an electronegative residue (e.g. glutamyl or aspartyl); or (d) a residue having a bulky side chain (e.g. phenylalanine) is substituted for (or by) one lacking a side chain (e.g., glycine).

Using these techniques, 800 samples from human subjects were screened for mutations in the cMLCK gene. Several mutations were identified, and are presented in Table 3.

One individual with MCV had a double point mutation, at cMLCK residues 87 and 95. The cDNA encoding this mutant cMLCK was isolated, cloned into a baculovirus vector, expressed in sF9 cells, and purified as described in Example 4. In cMLCK activity assays similar to those described in Example 15, this mutant showed enhanced ability to incorporate phosphate into RLC substrate, as manifested by an increased maximal velocity (about twice the maximal velocity of the unmutated enzyme).

Two true alleles were also identified. One, ala 89 glu, has an 8% prevalence in African-American populations. The other, pro 144 ala, has about 3% incidence in the general population.

TABLE 3

| cMLCK Amino acid residue | | |
|---|---|---|
| 87: | GCG ala | combined 87 and 95 mutation associated |
| mutated to: | CTG val | with MVCH; cMLCK with increased Vmax |
| 95: | GCA ala | |
| mutated to: | GAA glu | |
| 89: | GGC gly | allele, est 8% incidence in African Americans |
| mutated to: | GAC asp | |
| 144: | CCT pro | allele, est 3% incidence in general population |
| mutated to: | GCT ala | |

In a subsequence analysis, using these techniques, 300 African American patients with hypertension were evaluated for the presence of the ala 89 glu allele. Of this patient population, 25 individuals were heterozygous for the ala 89 glu allele, while one individual was homozyogous for the ala 89 glu allele. The homozygous individual had left ventricular hypertropy.

Variant cMLCK encoding sequences can be produced by standard DNA mutagenesis techniques, for example, M13 primer mutagenesis. Details of these techniques are provided in Sambrook et al. (In *Molecular Cloning: A Laboratory Manual*, CSHL, New York, 1989), Ch. 15. PCR-based and other mutagenesis techniques are also suitable. Details of some of these techniques are presented in Ausubel et al. (*Short Protocols in Molecular Biology,* 4th edition, Wiley, New York, 1999). By the use of such techniques, variants can be created which differ in minor ways from the human cMLCK sequences disclosed. DNA molecules and nucleotide sequences that are derivatives of those specifically disclosed herein, and which differ from those disclosed by the deletion, addition, or substitution of nucleotides while still encoding a protein that has at least 50% sequence identity with the cMLCK sequence disclosed (SEQ ID NO: 1), are comprehended by this invention. Also comprehended are more closely related nucleic acid molecules that share at least 60%, at least 75%, at least 80%, at least 90%, at least 95%, or at least 98% nucleotide sequence homology with the disclosed cMLCK sequences. In their most simple form, such variants may differ from the disclosed sequences by alteration of the coding region to fit the codon usage bias of the particular organism into which the molecule is to be introduced.

Alternatively, the coding region can be altered by taking advantage of the degeneracy of the genetic code to alter the coding sequence such that, while the nucleotide sequence is substantially altered, it nevertheless encodes a protein having an amino acid sequence substantially similar to the disclosed human cMLCK protein sequences. For example, the 87th amino acid residue from the amino-terminus of the human cMLCK protein is alanine. The nucleotide codon triplet GCG encodes this alanine residue. Because of the degeneracy of the genetic code, three other nucleotide codon triplets—GCT, GCC and GCA—also code for alanine. Thus, the nucleotide sequence of the human cMLCK ORF can be changed at this position to any of these three alternative codons without affecting the amino acid composition or characteristics of the encoded protein. Based upon the degeneracy of the genetic code, variant DNA molecules can be derived from the cDNA and gene sequences disclosed herein using standard DNA mutagenesis techniques as described above, or by synthesis of DNA sequences. Thus, this invention also encompasses nucleic acid sequences which encode a cMLCK protein, but which vary from the disclosed nucleic acid sequences by virtue of the degeneracy of the genetic code.

Variants of the cMLCK protein can also be defined in terms of their sequence identity with the prototype cMLCK protein shown in SEQ ID NO: 2. As described above, human cMLCK proteins share at least 50%, at least 60%, at least 75%, at least 80%, at least 90%, at least 95%, or at least 98% amino acid sequence identity with the human cMLCK protein disclosed herein (SEQ ID NO: 2). Nucleic acid sequences that encode such proteins can readily be determined simply by applying the genetic code to the amino acid sequence of an cMLCK protein, and such nucleic acid molecules can readily be produced by assembling oligonucleotides corresponding to portions of the sequence.

Nucleic acid molecules that are derived from the human cMLCK cDNA nucleic acid sequences disclosed include molecules that hybridize under stringent conditions to the disclosed prototypical cMLCK nucleic acid molecules, or fragments thereof. Specific non-limiting examples of stringent conditions are hybridization at 65° C. in 6×SSC, 5× Denhardt's solution, 0.5% SDS and 100 μg sheared salmon testes DNA, followed by 15-30 minute sequential washes at 65° C. in 2×SSC, 0.5% SDS, followed by 1×SSC, 0.5% SDS and finally 0.2×SSC, 0.5% SDS.

Low stringency hybridization conditions (to detect less closely related homologs) are performed as described above but at 50° C. (both hybridization and wash conditions); however, depending on the strength of the detected signal, the wash steps can be terminated after the first 2×SSC wash.

Human cMLCK nucleic acid encoding molecules (including SEQ ID NO: 1), and orthologs and homologs of these sequences can be incorporated into transformation or expression vectors.

EXAMPLE 4

Expression of cMLCK Locus Polypeptides

With the provision of the human cMLCK cDNA, the expression and purification of the cMLCK protein by standard laboratory techniques is now enabled. In addition, proteins or polypeptides encoded by the antisense strand of the cMLCK cDNA can likewise be expressed. After expression, the purified cMLCK locus protein or polypeptide can be used for functional analyses, antibody production, diagnostics, and patient therapy. Furthermore, the DNA sequence of the cMLCK cDNA and its antisense strand can be manipulated in studies to understand the expression of the gene and the function of its product, as well as the function of the associated cMLCK locus. Mutant forms of the human cMLCK can be isolated based upon information contained herein, and can be studied in order to detect alteration in expression patterns in terms of relative quantities, tissue specificity and functional properties of the encoded mutant cMLCK protein. Partial or full-length cDNA sequences, which encode for the subject protein, can be ligated into bacterial expression vectors. Methods for expressing large amounts of protein from a cloned gene introduced into *Escherichia coli* (*E. coli*) can be used for the purification, localization and functional analysis of proteins. For example, fusion proteins consisting of amino terminal peptides encoded by a portion of the *E. coli* lacZ or trpE gene linked to cMLCK proteins can be used to prepare polyclonal and monoclonal antibodies against these proteins (see below). Thereafter, these antibodies can be used to purify proteins by immunoaffinity chromatography, in diagnostic assays to quantitate the levels of protein and to localize proteins in tissues and individual cells by immunofluorescence.

Intact native protein can also be produced in *E. coli* in large amounts for functional studies. Methods and plasmid vectors for producing fusion proteins and intact native proteins in bacteria are described in Sambrook et al. (In *Molecular Cloning: A Laboratory Manual*, Ch. 17, CSHL, New York, 1989), and Ausubel et al. (*Short Protocols in Molecular Biology*, 4th edition, Chapter 16, Wiley, New York, 1999). Such fusion proteins can be made in large amounts, are easy to purify, and can be used to elicit antibody response. Native proteins can be produced in bacteria by placing a strong, regulated promoter and an efficient ribosome-binding site upstream of the cloned gene. If low levels of protein are produced, additional steps can be taken to increase protein production; if high levels of protein are produced, purification is relatively easy. Suitable methods are presented in Sambrook et al. (in *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989) and Ausubel et al. (*Short Protocols in Molecular Biology*, 4th edition, Chapter 16, Wiley, New York, 1999). Vector systems suitable for the expression of lacZ fusion genes include the pUR series of vectors (Ruther and Muller-Hill *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt *J. Mol. Biol.* 189:113, 1986). cMLCK fusion proteins can be isolated from protein gels, lyophilized, ground into a powder and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors can then be introduced into a variety of hosts including somatic cells, and simple or complex organisms, such as bacteria, fungi (Timberlake and Marshall, *Science* 244:1313-1317, 1989), invertebrates, plants (Gasser and Fraley, *Science* 244:1293, 1989), and animals (Pursel et al., *Science* 244:1281-1288, 1989), which cell or organisms are rendered transgenic by the introduction of the heterologous cMLCK cDNA.

For expression in mammalian cells, the cDNA sequence can be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct can be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) can be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al, *Proc. Natl. Acad. Sci USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, *A Manual of Methods for Baculovirus Vectors and Insect Cell Culture Procedures*, Texas Agricultural Experiment Station Bulletin No. 1555, 1987; Ausubel et al., Chapter 16 in *Short Protocols in Molecular Biology*, 1999) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg *Proc. Natl. Acad. Sci. USA* 78:2072-2076, 1981) or neo (Southern and Berg, *J. Mol. Appl. Genet* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J* 1:841, 1982), lipofection (Felgner et al., *Proc. Natl. Acad. Sci USA* 84:7413, 1987), DEAE dextran (McCuthan et al., *J. Natl. Cancer Inst* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). cMLCK encoding sequences can also be delivered to target cells in vitro via non-infectious systems, for instance liposomes.

These eukaryotic expression systems can be used for studies of cMLCK encoding nucleic acids and mutant forms of these molecules, the cMLCK protein and mutant forms of this protein. Such uses include, for example, the identification of regulatory elements located in the 5' region of the cMLCK gene on genomic clones that can be isolated from human genomic DNA libraries using the information contained in the present invention. The eukaryotic expression systems can also be used to study the function of the normal complete protein, specific portions of the protein, or of naturally occurring or artificially produced mutant proteins.

Using the above techniques, the expression vectors containing the cMLCK gene sequence or cDNA, or fragments or variants or mutants thereof, can be introduced into human cells, mammalian cells from other species or non-mammalian cells as desired. The choice of cell is determined by the purpose of the treatment. For example, monkey COS cells (Gluzman, *Cell* 23:175-182, 1981) that produce high levels of the SV40 T antigen and permit the replication of vectors containing the SV40 origin of replication can be used. Similarly, Chinese hamster ovary (CHO), mouse NIH 3T3 fibroblasts or human fibroblasts or lymphoblasts can be used.

The present invention thus encompasses recombinant vectors that comprise all or part of the cMLCK gene or cDNA sequences, or all or part of the antisense strand associated with the cMLCK-related locus, for expression in a suitable host. The cMLCK DNA is operatively linked in the vector to an expression control sequence in the recombinant DNA molecule so that the cMLCK polypeptide can be expressed. The expression control sequence can be selected from the group consisting of sequences that control the expression of genes of prokaryotic or eukaryotic cells and their viruses and combinations thereof. The expression control sequence can be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

In one embodiment, the host cell, which is transfected with the vector is selected from the group consisting of *E. coli, Pseudomonas, Bacillus subtilis, Bacillus stearothermophilus* or other *bacilli;* other bacteria; yeast; fungi; insect; mouse or other animal; or plant hosts; or human tissue cells.

It is appreciated that for mutant or variant cMLCK DNA sequences, similar systems are employed to express and produce the mutant product. In addition, fragments of the cMLCK protein are expressed essentially as detailed above. Such fragments include individual cMLCK protein domains or sub-domains, as well as shorter fragments such as peptides. cMLCK protein fragments having therapeutic properties can be expressed in this manner also.

It can be advantageous to express portions or fragments of the antisense strand of the cMLCK locus (as delineated by SEQ ID NO: 1), or of regions of the genome immediately upstream or especially immediately downstream of this locus, but which overlap the disclosed sequences.

The full length human cMLCK cDNA was subcloned into pVL1393 Baculovirus transfer vector under the polyhedrin promoter with a flag tag at 5' end of MLCK. The baculovirus containing MLCK gene was then constructed with the BaculoGold system (Pharmigen) from the transfer vector. The MLCK protein was expressed by infecting the virus into the SF9 insect cells and purified by anti-flag affinity agarose resin (Sigma). The purified MLCK was dialyzed into a buffer contain 10 mM MOPS, 0.5 mM EGTA, 0.2 M NaCl, 1 mM dithiothreitol (DTT), and 10% glycerol with final pH 7.0.

EXAMPLE 5

Suppression of cMLCK Locus Expression

A reduction of cMLCK locus protein expression in a transgenic cell can be obtained by introducing into cells an antisense construct based on the cMLCK locus (SEQ ID NO: 1), including, for example, the reverse complement of the cMLCK cDNA coding sequence, the cMLCK cDNA or gene sequence or flanking regions thereof. For antisense suppression, a nucleotide sequence from the cMLCK locus, e.g. all or a portion of the cMLCK cDNA or gene or the reverse complement thereof is arranged in reverse orientation relative to the promoter sequence in the transformation vector. Where the reverse complement of the reported sequences is used to suppress expression of proteins from the cMLCK locus, the sense strand of the disclosed cMLCK locus or cDNA is inserted into the antisense construct. Other aspects of the vector can be chosen as discussed above (Example 4).

The introduced sequence need not be the full length human cMLCK cDNA or gene or reverse complement thereof, and need not be exactly homologous to the equivalent sequence found in the cell type to be transformed. Generally, however, where the introduced sequence is of shorter length, a higher degree of homology to the native cMLCK locus sequence is needed for effective antisense suppression. In one embodiment, the introduced antisense sequence in the vector is at least 30 nucleotides in length, and improved antisense suppression is typically observed as the length of the antisense sequence increases. In another embodiment, the length of the antisense sequence in the vector is greater than 100 nucleotides. For suppression of the cMLCK gene itself, transcription of an antisense construct results in the production of RNA molecules that are the reverse complement of mRNA molecules transcribed from the endogenous cMLCK gene in the cell. For suppression of protein expression from the opposite strand of the cMLCK locus, transcription of an antisense construct results in the production of RNA molecules that are identical to the mRNA molecules transcribed from the endogenous cMLCK gene, assuming the antisense construct was generated from sequence within the cMLCK gene rather than in a flanking region. Antisense molecules made to target the sequence that is the reverse complement of the reported cMLCK locus serve to suppress any abnormal expression of proteins or peptides from the strand of the locus not encoding the cMLCK cDNA.

Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous cMLCK locus expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Finally, dominant negative mutant forms of the disclosed sequences can be used to block endogenous cMLCK activity. Peptides derived from the calmodulin-binding domain and neighboring residues are particularly likely to have inhibitory effects. For example, a peptide comprising the C-terminal 46 residues of cMLCK: NNLAEKAKRC NRRLKSQILL KKYLMKRRWK KNFIAVSAAN RFK-KISSSGA LMALGV (SEQ ID NO: 25) includes a consensus calmodulin binding domain and putative MLCK autoinhibitory region, and is predicted to be a strong peptide inhibitor of cMLCK.

Suppression of cMLCK expression or expression of other proteins or peptides encoded for by sequences within the cMLCK locus (including on the reverse complement of the cMLCK cDNA) can be, for instance, used to treat cardiomyopathy and other forms of cardiac dysfunction caused by abnormalities in the cMLCK locus.

EXAMPLE 6

Production of Specific Binding Agents

Monoclonal or polyclonal antibodies can be produced to either the normal cMLCK protein or mutant forms of this protein, as well as to proteins or peptides encoded for by the reverse complement of the disclosed cMLCK locus sequences. Optimally, antibodies raised against these proteins or peptides specifically detect the protein or peptide with which the antibodies are generated. That is, an antibody generated to the cMLCK protein or a fragment thereof recognizes and binds the cMLCK protein and does not substantially recognize or bind to other proteins found in human cells. Such antibodies can be produced that are specific for the phosphorylated form of human cardiac RLC, as well as fragments and variants of the phosphorylated form of human cardiac RLC.

The determination that an antibody specifically detects the cMLCK protein or phosphorylated human cardiac RLC is made by any one of a number of standard immunoassay methods; for instance, the Western blotting technique (Ausubel et al., *Short Protocols in Molecular Biology*, 4th edition, Chapter 10, Wiley, New York, 1999). To determine that a given antibody preparation (such as one produced in a mouse) specifically detects the cMLCK protein by Western blotting, total cellular protein is extracted from human cells (for example, cardiomyocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to a marker, such as an enzyme. In one embodiment, the enzyme is alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the cMLCK protein will, by this technique, be shown to bind to the cMLCK protein band (which will be localized at a position on the gel determined by its molecular weight). Non-specific binding of the antibody to other proteins can occur and may be detectable as a weak signal on the Western blot. The non-specific nature of this binding is recognized by the weak signal obtained on the Western blot relative to the strong primary signal arising from the specific antibody-cMLCK protein binding.

Substantially pure cMLCK protein or protein fragment (peptide) suitable for use as an immunogen can be isolated from the transfected or transformed cells as described above. Concentration of protein or peptide in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the cMLCK protein (or other proteins or peptides derived from the cMLCK locus) of identified and isolated as described can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogenous epitopes of a single protein are prepared by immunizing suitable animals with the expressed protein (Example 4), which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera Small doses (ng level) of antigen administered at multiple intradermal sites appear to be most reliable. An effective immunization protocol for rabbits can be found in Vaitukaitis et al. (*J. Clin. Endocrinol. Metab.* 33:988-991,1971).

Booster injections are given at regular intervals, and antiserum harvested when antibody titer thereof, as determined semi-quantitatively, for example, by double immunodiffusion in agar against known concentrations of the antigen, begins to fall. See, for example, Ouchterlony et al. (in *Handbook of Experimental Immunology*, Wier, D. (ed.) chapter 19. Blackwell, 1973). Plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against the subject cMLCK locus encoded proteins or peptides is to use one or more synthetic peptides synthesized on a commercially available peptide synthesizer based upon the predicted amino acid sequence of the cMLCK locus encoded protein or peptide.

By way of example only, polyclonal antibodies to specific peptides within cMLCK can be generated using well-known techniques, some of which are described in Ausubel et al. (*Short Protocols in Molecular Biology*, 4th edition, Chapter 11, Wiley, New York, 1999). Polyclonal antibodies are generated by injecting these peptides into a suitable animal, such as rabbits, chickens, or goats. The antibody preparations are used in immunolocalization and protein quantification studies of the cMLCK protein.

As a further example, polyclonal antibodies were raised against a phosphorylated peptide modeled after the human cardiac RLC phosphorylation site. A peptide with the sequence GANSNVF (SEQ ID NO:26), with the serine phosphorylated, was synthesized and injected into rabbit's using standard techniques as described above. No antibodies capable of specific binding to human cardiac RLC were obtained. Therefore, a concatamer duplicating the above sequence was synthesized: GANSNVFGANSNVF (SEQ ID NO:15), with two phosphoserines. This peptide was injected into rabbits, and yielded a highly specific polyclonal antibody which recognized human phosphorylated cardiac RLC, but did not recognize unphosphorylated human cardiac RLC, or phosphorylated RLC from mouse or rabbit. The antibody was used as described in examples 12 and 13.

D. Antibodies Raised by Injection of cMLCK Encoding Sequence

Antibodies can be raised against proteins and peptides of the cMLCK locus by subcutaneous injection of a DNA vector that expresses the desired protein or peptide, or a fragment thereof, into laboratory animals, such as mice. Delivery of the recombinant vector into the animals can be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose include those that express the cMLCK locus encoding sequence under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample; or for immunolocalization of the cMLCK protein.

For administration to human patients, antibodies, e.g., cMLCK specific monoclonal antibodies, can be humanized by methods known in the art. Antibodies with a desired binding specificity can be commercially humanized (Scotgene, Scotland, UK; Oxford Molecular, Palo Alto, Calif.).

EXAMPLE 7

Nucleic Acid-Based Diagnosis

One particular application of the cMLCK locus sequence information presented herein, and of the cMLCK cDNA sequence, is in the area of genetic testing for predisposition to cardiac dysfunction or cardiomyopathy owing to cMLCK locus deletion, genomic amplification or mutation. The gene sequence of the cMLCK gene, including intron-exon boundaries and associated 5' and 3' flanking regions, is also useful in such diagnostic methods. Individuals carrying mutations in the cMLCK locus or gene, or having amplifications or heterozygous or homozygous deletions of the cMLCK locus or gene, are detected at the DNA level with the use of a variety of techniques. For such a diagnostic procedure, a biological sample of the subject, which biological sample contains either DNA or RNA derived from the subject, is assayed for a mutated, amplified or deleted cMLCK locus or gene. Suitable biological samples include samples containing genomic DNA or RNA obtained from subject body cells, such as those present in peripheral blood, urine, saliva, tissue biopsy, surgical specimen, amniocentesis samples and autopsy material. The detection in the biological sample of a mutant cMLCK locus or gene, a mutant cMLCK RNA, or an amplified or homozygously or heterozygously deleted cMLCK locus or gene, is performed by one of a number of methodologies, for example, those described below.

A. Detection of Unknown Mutations:

Unknown mutations can be identified through polymerase chain reaction amplification of reverse transcribed RNA (RT-PCR) or DNA isolated from breast or other tissue, followed by direct DNA sequence determination of the products; single-strand conformational polymorphism analysis (SSCP) (for instance, see Hongyo et al., *Nucleic Acids Res.* 21:3637-3642, 1993); chemical cleavage (including HOT cleavage) (Bateman et al., *Am. J. Med. Genet.* 45:233-240, 1993; reviewed in Ellis et al., *Hum. Mutat.* 11:345-353, 1998); denaturing gradient gel electrophoresis (DGGE), ligation amplification mismatch protection (LAMP); or enzymatic mutation scanning (Taylor and Deeble, *Genet. Anal* 14:181-186, 1999), followed by direct sequencing of amplicons with putative sequence variations.

B. Detection of Known Mutations:

The detection of specific known DNA mutations can be achieved by methods such as hybridization using allele specific oligonucleotides (ASOs) (Wallace et al., CSHL Symp. Quant. Biol. 51:257-261, 1986), direct DNA sequencing (Church and Gilbert, *Proc. Natl. Acad. Sci. USA* 81:1991-1995, 1988), the use of restriction enzymes (Flavell et al., *Cell* 15:25, 1978; Geever et al., 1981), discrimination on the basis of electrophoretic mobility in gels with denaturing reagent Myers and Maniatis, Cold Spring Harbor Symp. Quant. Biol. 51:275-284, 1986), RNase protection (Myers et al., *Science* 230:1242, 1985), chemical cleavage (Cotton et al, *Proc. Natl. Acad. Sci. USA* 85:4397-4401, 1985), and the ligase-mediated detection procedure (Landegren et al., *Science* 241:1077, 1988). Oligonucleotides specific to normal or mutant cMLCK sequences are chemically synthesized using commercially available machines. These oligonucleotides are then labeled radioactively with isotopes (such as $^{32}P$) or non-radioactively, with tags such as biotin (Ward and Langer et al., *Proc. Natl. Acad. Sci. USA* 78:6633-6657, 1981), and hybridized to individual DNA samples immobilized on membranes or other solid supports by dot-blot or transfer from gels after electrophoresis. These specific sequences are visualized by methods such as autoradiography or fluorometric (Landegren et al., *Science* 242:229-237, 1989) or colorimetric reactions (Gebeyehu et al., *Nucleic Acids Res.* 15:4513-4534, 1987). Using an ASO specific for a normal allele, the absence of hybridization indicates a mutation in the particular region of the gene, or deleted cMLCK gene. In contrast, if an ASO specific for a mutant allele hybridizes to a clinical sample then that indicates the presence of a mutation in the region defined by the ASO.

C. Detection of Genomic Amplification or Deletion:

Gene dosage (copy number) can be important in neoplasms; it is therefore advantageous to determine the number of copies of cMLCK locus nucleic acids in samples of tissue, e.g. cardiac tissue. It can also be advantageous to determine the copy number of certain portions of the disclosed nucleic acids, for instance about the 3'-terminal half or the 3'-terminal third of the disclosed cMLCK cDNA (SEQ ID NO: 1), or of the 5' or especially 3' region of the gene can also be determined. Probes generated from the disclosed encoding sequence of cMLCK (cMLCK probes or primers), or the reverse complement of the cMLCK encoding sequence, can be used to investigate and measure genomic dosage in the q23 region of chromosome 17, and more particularly in the cMLCK gene.

In one embodiment, the cMLCK locus is divided into shorter regions and only certain regions are probed for amplification. By way of example, the human cMLCK locus, cDNA, ORF, coding sequence and gene sequences is apportioned into about halves or quarters based on sequence length, and the isolated nucleic acid molecules (e.g., oligonucleotides) is derived from the first or second halves of the molecules, or any of the four quarters. For example, the portion of the prototypical human cMLCK cDNA shown in SEQ ID NO: 1 is 1791 nucleotides in length and so can be divided into about halves (e.g., from about nucleotides 1-885 and from about nucleotides 886-1791) or about quarters (1-447, 448-885, 886-1343 and 1344-1791). The cDNA also could be divided into smaller regions, e.g. about eighths, sixteenths, twentieths, fiftieths and so forth, with similar effect. Another mode of division is to select the 5' (upstream) and/or 3' downstream region associated with the cMLCK cDNA or cMLCK gene.

Appropriate techniques for measuring gene dosage are known in the art; see for instance, U.S. Pat. No. 5,569,753 ("Cancer Detection Probes") and Pinkel et al. (*Nat. Genet.* 20:207-211, 1998) ("High Resolution Analysis of DNA Copy Number Variation using Comparative Genomic Hybridization to Microarrays").

Determination of gene copy number in cells of a patient-derived sample using other techniques is known in the art. For example, cMLCK amplification in muscle-derived cell lines as well as uncultured cardiomyocytes or other cells is carried out using bicolor FISH analysis. By way of example, interphase FISH analysis of cardiomyocytes is carried out as previously described (Barlund et al., *Genes Chromo. Cancer* 20:372-376, 1997). The hybridizations are evaluated using a Zeiss fluorescence microscope. Approximately 20 non-overlapping nuclei with intact morphology based on DAPI counterstain are scored to determine the mean number of hybridization signals for each test and reference probe.

For tissue microarrays, the FISH is performed as described in Kononen et al., *Nat. Med.* 4:844-847, 1998. Briefly, consecutive sections of the array are deparaffinized, dehydrated in ethanol, denatured at 74° C. for 5 minutes in 70% formamide/2×SSC, and hybridized with test and reference probes. The specimens containing tight clusters of signals or >3-fold increase in the number of test probe as compared to control are considered as amplified. Microarrays are constructed as described in WO9944063A2 and WO9944062A1.

In another embodiment, overexpression of the cMLCK gene is detected by measuring the cellular level of cMLCK-specific mRNA. mRNA can be measured using techniques well known in the art, including for instance Northern analysis, RT-PCR and mRNA in situ hybridization.

The nucleic acid-based diagnostic methods of this invention can be predictive of susceptibility to cardiac dysfunction and/or cardiomyopathy.

EXAMPLE 8

Protein-Based Diagnosis

An alternative method of diagnosing cMLCK locus or gene amplification, deletion or mutation, as well as abnormal cMLCK expression, is to quantitate the level of cMLCK locus-associated protein (for instance, cMLCK protein) in the cells of an individual. This diagnostic tool is useful for detecting reduced levels of the cMLCK locus-associated protein which result from, for example, mutations in the promoter regions of the cMLCK gene or mutations within the coding region of the gene which produced truncated, non-functional or unstable polypeptides, as well as from deletions of a portion of or the entire cMLCK gene. Alternatively, duplications of the cMLCK locus can be detected as an increase in the expression level of one or more cMLCK locus-associated proteins. Such an increase in protein expression can also be a result of an up-regulating mutation in the promoter region or other regulatory or coding sequence within the cMLCK locus or cMLCK gene. Localization and/or coordinated cMLCK expression (temporally or spatially) can also be examined using well known techniques. The determination of reduced or increased cMLCK locus-associated protein levels (e.g., cMLCK or proteins or peptides expressed from the cMLCK locus for instance from the reverse complement of the cMLCK cDNA or gene sequence), in comparison to such expression in a normal cell, would be an alternative or supplemental approach to the direct determination of cMLCK locus deletion, amplification or mutation status by the methods outlined above and equivalents. The availability of antibodies specific to cMLCK locus protein(s) will facilitate the detection and quantitation of cellular cMLCK locus protein(s) by one of a number of immunoassay methods which are well known in the art and are presented in Harlow and Lane (*Antibodies, A Laboratory Manual*, CSHL, New York, 1988). Methods of constructing such antibodies are discussed above, in Example 6, and antibodies are described in Example 12.

Any immunoassay format (e.g., ELISA, Western blot, or RIA assay) can be used to measure cMLCK locus polypeptide or protein levels; comparison is to wild-type (normal) cMLCK levels, and an increase in cMLCK polypeptide is indicative of an abnormal biological condition such as neoplasia immunohistochemical techniques can also be used for cMLCK polypeptide or protein detection. For example, a tissue sample is obtained from a subject, and a section stained for the presence of cMLCK using a cMLCK specific binding agent (e.g., anti-cMLCK antibody) and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantitating a cMLCK locus protein, a biological sample of the subject, which sample includes cellular proteins, is used. Such a biological sample can be obtained from body cells, particularly cardiomyocytes. Quantitation of cMLCK locus protein is achieved by immunoassay and compared to levels of the protein found in healthy cells. A significant (for example, about a 30% or greater) reduction in the amount of cMLCK locus protein in the cells of a subject compared to the amount of cMLCK protein found in normal human cells could be taken as an indication that the subject may have deletions or mutations in the cMLCK gene locus, whereas a significant (for example, about a 30% or greater) increase would indicate that a duplication (amplification) may have occurred. Deletion, mutation and/or amplification of or within the cMLCK locus, and substantial under- or over-expression of one or more cMLCK locus protein(s), may indicate cardiac dysfunction or a predilection to cardiac dysfunction or cardiomyopathy.

EXAMPLE 9 cMLCK Knockout and Overexpression Transgenic Animals

Mutant organisms that under-express or over-express cMLCK or another cMLCK locus associated protein are useful for research Such mutants allow insight into the physiological and/or pathological role of cMLCK in a healthy and/or pathological organism. These mutants are "genetically engineered," meaning that information in the form of nucleotides has been transferred into the mutant's genome at a location, or in a combination, in which it would not normally exist. Nucleotides transferred in this way are said to be "non-native." For example, a non-cMLCK promoter inserted upstream of a native cMLCK gene would be non-native. An extra copy of a cMLCK gene on a plasmid, transformed into a cell, would be non-native.

Mutants can be, for example, produced from mammals, particularly non-human mammals, such as mice, that either over-express cMLCK or under-express cMLCK or another cMLCK locus associated protein, or that do not express cMLCK at all. Over-expression mutants are made by increasing the number of cMLCK genes in the organism, or by introducing an cMLCK gene into the organism under the control of a constitutive or viral promoter such as the mouse mammary tumor virus (MMTV) promoter; a muscle-specific promoter such as the cardiac ELC promoter (Vermuri et al., PNAS 96: 1048-1053, 1999); or the metallothionein promoter. Mutants that under-express cMLCK can be made by using an inducible or repressible promoter, or by deleting the cMLCK gene, or by destroying or limiting the function of the cMLCK gene, for instance by disrupting the gene by transposon insertion.

Antisense genes can be engineered into the organism, under a constitutive or inducible promoter, to decrease or prevent cMLCK locus expression, as discussed above in Example 5.

A gene is "functionally deleted" when, for example, genetic engineering has been used to negate or reduce gene expression to negligible levels. When a mutant is referred to in this application as having the cMLCK gene altered or functionally deleted, this refers to the cMLCK gene and to any ortholog of this gene. When a mutant is referred to as having "more than the normal copy number" of a gene, this means that it has more than the usual number of genes found in the wild-type organism, e.g. in the diploid mouse or human.

A mutant mouse over-expressing cMLCK is made by constructing a plasmid having the cMLCK gene driven by a promoter, such as the mouse mammary tumor virus (MMTV) promoter or the cardiac ELC2 promoter. In one embodiment, this plasmid is introduced into mouse oocytes by microinjection. The oocytes are implanted into pseudopregnant females, and the litters are assayed for insertion of the transgene. Multiple strains containing the transgene are then available for study.

An inducible system can be created in which the subject expression construct is driven by a promoter regulated by an agent that can be fed to the mouse, such as tetracycline. Such techniques are well known in the art (see, e.g., Pinkert et al., *Transgenic Animal Technology: A Laboratory Handbook*, Academic Press, San Diego, 1994).

A mutant knockout animal (e.g., mouse) from which a cMLCK locus gene is deleted is made by removing coding regions of the cMLCK gene from embryonic stem cells. The methods of creating deletion mutations by using a targeting vector have been described (Thomas and Capecchi, *Cell* 51:503-512, 1987; Pinkert et al., supra).

EXAMPLE 10

Transfer of cMLCK Sequences

Approaches for combating cardiac dysfunction and/or cardiomyopathy in subjects are disclosed herein.

Retroviruses have been considered a preferred vector for experiments in the transfer of nucleic acids in vivo, with a high efficiency of infection and stable integration and expression (Orkin et al., *Prog. Med. Genet.* 7:130-142, 1988). The full-length cMLCK locus or gene or cDNA can be cloned into a retroviral vector and driven from either its endogenous promoter or from the retroviral LTR (long terminal repeat). Other viral transfection systems may also be used for this type of approach, including adenovirus, adeno-associated virus (AAV) (McLaughlin et al., *J. Virol.* 62:1963-1973, 1988), Vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

Recent developments in gene therapy techniques include the use of RNA-DNA hybrid oligonucleotides, as described by Cole-Strauss, et al. (*Science* 273:1386-1389, 1996). This technique allows for site-specific integration of cloned sequences, thereby permitting accurately targeted gene replacement.

In addition to delivery of cMLCK to cells using viral vectors, it is possible to use non-infectious methods of delivery. For instance, lipidic and liposome-mediated gene delivery has recently been used successfully for transfection with various genes (for reviews, see Templeton and Lasic, *Mol. Biotechnol.* 11:175-180, 1999; Lee and Huang, *Crit. Rev. Ther. Drug Carrier Syst.* 14:173-206; and Cooper, *Semin. Oncol.* 23:172-187, 1996). For instance, cationic liposomes have been analyzed for their ability to transfect monocytic leukemia cells, and shown to be a viable alternative to using viral vectors (de Lima et al., *Mol. Membr. Biol.* 16:103-109, 1999). Such cationic liposomes can also be targeted to specific cells through the inclusion of, for instance, monoclonal antibodies or other appropriate targeting ligands (Kao et al., *Cancer Gene Ther.* 3:250-256, 1996).

To reduce the level of cMLCK expression, gene therapy can be carried out using antisense or other suppressive constructs, the construction of which is discussed above (Example 5).

EXAMPLE 11

Diagnostic Kits

Kits are provided herein which contain the necessary reagents for determining gene copy number (genomic amplification), such as probes or primers specific for the cMLCK gene, as well as written instructions. The instructions can provide calibration curves or charts to compare with the determined (e.g., experimentally measured) values. Kits are also provided to determine elevated expression of mRNA (i.e., containing probes) or cMLCK locus-associated protein (ie., containing antibodies or other cMLCK-protein specific binding agents).

A. Kits for Detection of cMLCK Genomic Amplification

The nucleotide sequences disclosed herein, and fragments thereof, can be supplied in the form of a kit for use in detection of cMLCK locus genomic amplification and/or diagnosis of cardiac dysfunction or cardiomyopathy. In such a kit, an appropriate amount of one or more of the cMLCK-specific oligonucleotide primers is provided in one or more containers. In one embodiment, the oligonucleotide primers are provided suspended in an aqueous solution or as a freeze-dried or lyophilized powder. The container(s) in which the oligonucleotide(s) are supplied can be any conventional container that is capable of holding the supplied form, for instance, microfuge tubes, ampoules, or bottles. In some applications, pairs of primers are provided in pre-measured single use amounts in individual, typically disposable, tubes or equivalent containers. With such an arrangement, the sample to be tested for the presence of cMLCK locus genomic amplification is added to the individual tubes and in vitro amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR in vitro amplification reactions. Those of ordinary skill in the art know the amount of oligonucleotide primer that is appropriate for use in a single amplification reaction. General guidelines may for instance be found in Innis et al. (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and Ausubel et al. (In *Current Protocols in Molecular Biology*, John Wiley & Sons, New York, 1998). Alternative amplification methods may also be used (such as strand displacement amplification—U.S. Pat. Nos. 5,744,311, 5,648,211, and 5,631,147).

A kit can include more than two primers, in order to facilitate the PCR in vitro amplification of cMLCK locus genomic sequences, for instance the cMLCK gene or the 5' or 3' flanking region thereof.

In some embodiments of the current invention, the kits also include the reagents necessary to carry out PCR in vitro amplification reactions, including, for instance, DNA sample preparation reagents, appropriate buffers (e.g., polymerase buffer), salts (e.g., magnesium chloride), and deoxyribonucleotides (dNTPs). Written instructions can also be included.

In another embodiment, kits include either labeled or unlabeled oligonucleotide probes for use in detection of the in vitro amplified cMLCK locus sequences. The appropriate sequences for such a probe is any sequence that falls between the annealing sites of the two provided oligonucleotide primers, such that the sequence the probe is complementary to is amplified during the PCR reaction.

One or more control sequences for use in the PCR reactions can also be provided in the kit. The design of appropriate positive control sequences is well known to one of ordinary skill in the appropriate art.

B. Kits For Detection of mRNA Overexpression

Kits similar to those disclosed above for the detection of cMLCK locus genomic amplification can be used to detect cMLCK locus-associated mRNA overexpression. Such kits include an appropriate amount of one or more of the oligonucleotide primers for use in reverse transcription PCR reactions, similarly to those provided above, with art-obvious modifications for use with RNA.

In some embodiments of the current invention, kits for detection of cMLCK mRNA overexpression include the reagents necessary to carry out RT-PCR in vitro amplification reactions, including, for instance, RNA sample preparation reagents (including e.g., an RNAse inhibitor), appropriate buffers (e.g. polymerase buffer), salts (e.g., magnesium chloride), and deoxyribonucleotides (dNTPs). Written instructions can also be included.

Kits in addition can include either labeled or unlabeled oligonucleotide probes for use in detection of the in vitro amplified target sequences. The appropriate sequences for such a probe is any sequence that falls between the annealing sites of the two provided oligonucleotide primers, such that the sequence the probe is complementary to is amplified during the PCR reaction.

In another embodiment, the kit includes one or more control sequences for use in the RT-PCR reactions. The design of appropriate positive control sequences is well known to one of ordinary skill in the appropriate art.

Alternatively, kits can be provided with the necessary reagents to carry out quantitative or semi-quantitative Northern analysis of cMLCK locus mRNA. Such kits include, for example, at least one cMLCK-specific oligonucleotide for use as a probe. This oligonucleotide can be labeled in any conventional way, including with a selected radioactive isotope, enzyme substrate, co-factor, ligand, chemiluminescent or fluorescent agent, hapten, or enzyme label.

C. Kits For Detection of cMLCK Locus Protein or Peptide Overexpression

Kits for the detection of cMLCK locus-associated protein overexpression, for instance cMLCK protein overexpression, are also encompassed in the current invention. Such kits include at least one target (e.g., cMLCK) protein specific binding agent (e.g. a polyclonal or monoclonal antibody or antibody fragment). In one embodiment, the kit includes at least one control. The cMLCK protein specific binding agent and control are contained in separate containers. Optionally, the kits can also include a means for detecting cMLCK:agent complexes, for instance the agent can be detectably labeled. If the detectable agent is not labeled, it can be detected by second antibodies or protein A for example which can also be provided in one or more separate containers.

Additional components in a kit includes instructions for carrying out the assay. Instructions will allow the tester to determine whether cMLCK expression levels are elevated. Optionally, reaction vessels and auxiliary reagents such as chromogens, buffers, enzymes, etc. can also be included in the kits.

EXAMPLE 12

Specific Antibodies Reacting with Phosphorylated Human and Mouse RLC

To study phosphorylation of RLC by cardiac MLCK, a polyclonal antibody was raised against peptides containing the RLC serine residue which is phosphorylated by MLCK Peptides were synthesized containing this serine residue in its phosphorylated state, with the bilateral flanking 3 residues on either side. Both the mouse and human sequences were synthesized. These were injected into rabbits as described in Example 6.

After an initial attempt to raise a useable antibody failed, inoculation of a rabbit with a concatamer of 2 such peptides (SEQ ID NO: 15) produced surprisingly specific antibodies. Two polyclonal antibodies were made: one against human and another against murine sequence.

On Western blot, both anti-human RLC-P and anti-mouse RLC-P polyclonal antibodies detected only the phosphorylated human cardiac RLC. The antibody against human peptide sequence was specific for human phosphorylated cardiac RLC, while the antibody against murine sequence reacted against rabbit, murine and human phosphorylated cardiac RLC.

Cryosections of fresh human skeletal muscle tissue were prepared as described in Ausubel et al., Chapter 14 of *Short Protocols in Molecular Biology*, 1999. Immunohistochemistry was performed using fluorescently labeled anti-rabbit secondary antibodies as described in Ausubel et al.

When the antibody against the phosphorylated human RLC was used as the primary antibody, a mixture of distinct myofibers with and without RLC phosphorylation was observed. The pattern of staining did not resemble motor units. Co-staining with antibodies to fast myosin showed that both fast and slow myofibers contained RLC-P detected with this antibody.

In order to confirm this finding, the antibody raised against the murine phosphorylated RLC peptide was used for immunohistochemical analysis of a variety of mouse and rabbit skeletal muscle cryosections. In each case, a patchy pattern of phosphorylated and non-phosphorylated fibers similar to the human sample was observed. In order to confirm the heterogeneous pattern RLC phosphorylation in skeletal muscle, individual muscle fibers from rabbit psoas muscle were evaluated on a 10% glycerol gel that resolves phosphorylated RLC from non-phosphorylated fibers. Consistent with the immunohistochemical findings, the gel analysis showed fibers with and without detectable RLC phosphorylation.

EXAMPLE 13

Distribution of Phosphorylated RLC and cMLCK in the Heart

In order to study the pattern of phosphorylated RLC in mouse heart, the antibody against the murine phosphorylated RLC described in example 12 was used for immunohistochemical analysis of cryosections from murine hearts. In all cases, the maximal staining occurred at the apex and contrasted with significantly less staining in the mid-region of the ventricles and the papillary muscles. An intermediate intensity of staining was observed at the base. In addition, a gradient of expression (from greatest to least) was observed extending inward from epicardium to endocardium. Technical artifact was ruled out using other antibodies that showed uniform staining throughout the heart. Western blot analysis with tissue from apex, epicardium, endocardium, and papillary muscle probed with the same antibody confirmed the non-uniform pattern of expression that was observed in immunohistochemical analysis.

In order to study the distribution of the MLCK cloned from human heart, a polyclonal antibody to the entire human protein was produced. The full length cDNA encoding the human MLCK protein was inserted into a baculoviral vector that was transfected with helper virus to produce the recombinant baculovirus which in turn was used to infect sF9 cells (see Example 4 for details of expression and purification). A FLAG® tag (kodak), placed at the amino-terminal end of the MLCK permitted affinity column purification directly from the SF9 cell homogenate. Rabbits were innoculated with this affinity purified protein and boosted at 2, 4, and 6 weeks. The 8 and 10 week serum was affinity purified using affinity chromatography with full-length cMLCK. The serum from one rabbit detected the expressed human MLCK on Western blot although it was less useful for fluorescent in situ detection of MLCK in fresh-frozen mouse heart.

Western blot analysis was performed on tissue from mouse and rabbit hearts that were fresh frozen in super-cooled isopentane. Five micron sections from apex, epicardium, endocardium and inter-ventricular septum were collected and pooled from multiple hearts. MLCK was extracted separately from these regions and analyzed by Western blot. A matched Western blot performed on extracted myosin from similarly obtained tissue was probed with the antibody to phosphorylated murine RLC. The Western blot analysis of both murine and rabbit heart tissue showed a regional distribution of the MLCK that matched the distribution of phosphorylaied RLC as detected by both fluorescent in situ studies and western blot analysis.

The non-uniform but reproducible staining pattern is inversely related to the pattern of hypertrophy in humans with mid-cavitary ventricular hypertrophy (MCV), and in mice expressing a human ELC mutant protein associated with MCV (Met149Val). Specifically, anti-MLC-P immunohistochemistry revealed strong staining of the apex, intermediate staining at the base, and light staining of the mid-ventricular myocardium and papillary muscle. Anti-cMLCK Western blot revealed the same pattern.

It has previously been shown that transgenic mice expressing a human mutant ELC (Met149Val) faithfully reproduced the MCV phenotype of patients from whom the mutant ELC was derived. By comparing the pattern of cardiac hypertrophy in M149V mice with the pattern of RLC phosphorylation in the normal mouse heart, it is observed that the normally hypo-phosphorylated portion of the heart is the very region that hypertrophies in mice expressing the mutant ELC throughout the heart. In other words, the mid-ventricular areas of light immunohistochemical staining correspond exactly to the pattern of MCV observed in humans and transgenic mice expressing mutant ELC.

EXAMPLE 14

Muscle Mechanics

The effects of mutations in human cMLCK can be investigated by examining myocardial mechanics in right ventricular papillary muscles obtained from transgenic mice. Mice can be constructed expressing a human cMLCK, and mutant human cMLCK, or mutant human RLC (such as ala 13 thr and glu 22 lys, as described in Poetter et al., Nature Genetics 13: 63-69, 1996). Methods for examining myocardial mechanics of normal and mutant mice may be found in Vemuri et al., PNAS 96: 1048-1053, 1999, which is herein incorporated by reference in its entirety. These methods are reviewed in this Example.

Mice are killed, and the hearts are rapidly excised. The right ventricles are opened, and the papillary muscles are excised and pinned into a dish containing a high EGTA permeabiling solution (Eastwood et al., *Tissue Cell* 11, 553-566, 1979) maintained at 2° C. After 4 hours, the solution is replaced by one containing 50% glycerol and is kept at 20° C.

Measurement Apparatus. Each muscle strip examined is mounted between a silicon strain gauge force transducer and a servo motor in a temperature-controlled chamber at 20° C., with a low calcium concentration (relaxing) solution. The system has a force transducer element (Akers, Horten, Norway) with custom mounting, which has a natural resonance at 5.6 kHz but, with damping, has a flat frequency response up to 3 kHz. The frequency response of the servo motor (6350; Cambridge Technology, Cambridge, Mass.) is limited by a resonance at 1300 Hz. Control of muscle length is performed by using custom software written in the inventor's laboratory. The software controls a programmable filter (9002; Frequency Devices, Haverhill, Mass.) and a digital oscilloscope (model 54600A; Hewlett-Packard). Data consisting of force and motor position (hence muscle length) are sampled by using an A/D board (DT2828; Data Translation, Marlboro, Mass.) with 12 bits of resolution at a frequency of 5 kHz for quick stretch experiments. For dynamic stiess measurements, the sampling frequency varies from 16 kHz at the high driving frequencies down to 40 Hz at a driving frequency of 0.02 Hz. The programmable filter (8 pole Bessel with linear phase) is set to low pass filter at a frequency $\frac{1}{8}$ (at high frequencies) to $\frac{1}{64}$ (at lower frequencies) of the data acquisition rate to avoid aliasing. Data are collected over 256 sinusoidal cycles at 500 Hz and over 1 cycle at 0.02 Hz, saved on an 80486 computer and are analyzed off-line.

Muscle Protocol. The muscle fibers are mounted and stretched in relaxing solution to 110% of slack length. Muscle dimensions are measured optically under a dissecting microscope. Under computer control, the servo motor is driven sinusoidally at 55 selected frequencies from 500 Hz to 0.02 Hz. The length changes chosen are 0.1% muscle length, but amplitudes between 0.05 and 0.5% should give similar results. The sinusoidal amplitude of 0.1% is as small as technically feasible to minimize the nonlinearities of viscoelastic tissues. The signals representing motor position (muscle fiber length) and force are digitized and recorded to computer disk. Then, the bathing solution is changed briefly to a "preactivating solution" similar to the relaxing solution but with 20 mM 1,6-hexamethylenediamine-N,N,N'N'-tetraacetic acid replacing the EGTA. It then is changed to a high calcium solution of the following composition, in mM: Na 51, K 86, Cl 13, creatine phosphate 20, EGTA 25, N-Tris[hydroxymethyl]methyl-2-aminoethanesulfonic acid 100, MGATP 5, reduced glutathione 10, leupeptin 0.1, and sufficient CAEGTA to obtain a pCa of 4.3. After steady isometric force is reached, the muscle is step-wise stretched to 1% of its initial length, and the force signal is recorded for 4 s. Then, the motor again is driven at each of 55 discrete frequencies between 500 Hz and 0.02 Hz, and the motor position and force signals are recorded. The bathing solution is replaced with an identical solution without any ATP or creatine phosphate with a flow-through wash of >5× the chamber volume. The dynamic stiffness again is determined in this rigor solution.

Data analysis can include determining the isometric force before any stretches, displaying the force levels during the 1% step-wise stretch, and measuring the time-to-peak of the delayed force, the amplitude of the delayed force, and the force amplitude for 4 s of stretch. Initial isometric force is normalized to cross-sectional area to give stress ($kN/m^2$). To compare the quick stretch experimental data, forces during these stretches are normalized to initial isometric prestretch force. During the experiments in which the fiber bundles were sinusoidally lengthened and shortened, the signals representing the changing fiber length and the force were collected for each of the discrete frequencies.

The fast Fourier transform can be used on the length signal to determine the driving frequency of the length oscillation, and its amplitude and phase. At this driving frequency, the fast Fourier transform of the force signal is computed to determine the force oscillation amplitude and phase. The response of the fibers is computed as the ratio of the force amplitude to length amplitude (modulus, or stiffness) and the force phase minus the length phase. The impedance at each frequency consists of both the magnitude ratio and phase. These transforms are computed at each frequency for each condition (relaxed, activated, and rigor). Thus, correction for the fiber response to series viscoelasticities (measured as end-compliance) is accomplished through analysis of rigor fibers preloaded to the tension of the activated fiber. Parallel viscoelasticities are determined in fibers under relaxed conditions and are subtracted from the activated response.

Effect of RLC Phosphorylation in Skinned Muscle Fibers

The effect of regulatory light chain phosphorylation on stretch activation was investigated in chemically skinned muscle fibers from rabbit. This experimental model is well established in the art, and the model with various modifications is described in detail in U.S. Pat. No. 5,446,186; Davis, Advances in Experimental Medicine & Biology 453: 343-51, 1998; Rapp et al., Journal of Muscle Research & Cell Motility 17: 617-29, 1996; Davis et al., Biophysical Journal. 68: 2032-40, 1995; Davis et al., PNAS 92: 10482-10486, 1995; and Davis et al., *Biophysical Journal* 65: 1886-1898, 1993; all of which are herein incorporated by reference.

The human cMLCK was expressed in sF9 cells and purified as described in Example 4. The purified cMLCK protein was activated by combining in solution with calcium-calmodulin, and used to phosphorylate myosin RLCs in the skinned muscle preparation. Control preparations were treated with solution without cMLCK.

These fibers were subjected to large stretches (0.4-0.8% muscle lengths) before and after RLC phosphorylation. Prior to stretch there is a dramatic increase in isometric tension produced by the RLC phosphorylated fibers (RLCP) compared to the same fiber before RLC phosphorylation. On average there is a 2.5 fold increase in isometric fiber tension, from a baseline of 22% maximal tension to 56% of the maximal value. Consequently the tension increases from stretch and the ensuing tension transient is noticeably greater in the RLCP containing fibers than in the non-phosphorylated RLC fibers. However, the relative total excursion (the sum of the fall and subsequent delayed rise in tension) that occurs following the initial tension increase is proportionally greater in the RLC (17%) vs. RLCP (10%). The increased total excursion represents a 7% larger stretch-activation response in the fibers with the non-phosphorylated RLC. Relaxation kinetics studies, that impose small step-stretches on these fibers, have shown that the stretch-activation response (HuxleySimmons phase 3) is disproportionately increased in fibers without phosphorylated RLC (manuscript submitted). Thus, in small as well as large stretch studies, the increased tension produced by RLCP is associated with a reciprocal drop in the stretch-activation response while the converse effect occurs in non-phosphorylated fibers. These mechanical differences, associated with the gradient of RLC phosphorylation across the ventricular wall, support the complex pattern of cardiac torsion.

EXAMPLE 15

Methods of Screening for Compounds That Modulate cMLCK Activity

The reagents provided in this disclosure form the basis of a variety of assays that can be used to identifying compounds that modulate cMLCK activity. Such modulatory compounds may be, for example, pharmaceuticals, peptides, or antibodies, and may increase or decrease cMLCK activity.

In Vitro Assays for Myosin Light Chain Kinase Biological Activity

For example, a kinase activity assay is run in the presence and absence of the test compound, and the impact of the compound on cMLCK's ability to phosphorylate a suitable substrate is determined. Such assays for MLCK kinase biological activity are well-known in the art; see, for example, U.S. Pat. No. 5,906,819; Ausubel et al., Short Protocols in Molecular Biology, 4th edition at p. 17-22. To assess the ability of a putative cMLCK modulatory compound to inhibit or activate cMLCK, a series of kinase activity assays are carried out in the presence of varying concentrations of the putative modulatory compound (including zero concentration), and the extent of phosphate incorporation into substrate is determined for each assay.

For example, the kinase reaction for myosin light chain kinase is carried out in 50 µl of reaction mixture (50 mM Tris/HCl at pH 7.5, 1 mM $Mg_{Cl2}$, 85 M KCl, 500 mM ATP, purified cMLCK (typically from 0.1 to 100 ng of protein depending on reaction conditions), and myosin light chain, a myosin light chain fragment or variant, or a synthetic peptide substrate capable of being phosphorylated by cMLCK and specifically recognized by an anti-human RLC-P antibody when phosphorylated. An example of a suitable synthetic peptide substrate, based on the sequence surrounding the phosphorylatable serine of human cardiac MLC, is GGANSNVFSMFEQT (SEQ ID NO: 16). Reactions is initiated by addition of enzyme or substrate. Incubation period is determined empirically based on a variety of factors including enzyme and substrate concentration and incubation temperature. Commonly used conditions are about 10 minutes of incubation at about 30° C. Reactions are carried out with or without 0.1 mM $Ca_{Cl2}$ and 10 µg/ml calmodulin. Duplicate reactions are carried out with or without the compound being tested. Reactions are stopped by adding a calcium chelator such as 1 mM EGTA, and/or addition of sodium dodecyl sulfate as described in U.S. Pat. No. 5,906,819. Once the reaction is stopped, the extent of substrate phosphorylation in each reaction is determined.

Another suitable example protocol is described in Ausubel et al., *Short Protocols in Molecular Biology,* 4th Edition at p. 17-22, and is similar to the protocol in U.S. Pat. No. 5,906,819. The following modifications are made to adapt the assay for determination of myosin light chain kinase biological activity: the synthetic peptide substrate described in the Ausubel et al. Protocols is replaced by a like amount of myosin light chain, a myosin light chain fragment or variant, or a synthetic peptide substrate capable of being phosphorylated by cMLCK and specifically recognized by an anti-human RLC-P antibody when phosphorylated. The calmodulin-dependent kinase used is cMLCK. After the reaction is stopped, the mixture is spotted onto phosphocellulose P81 if a short peptide substrate; or nitrocellulose, PVDF, and the like if the substrate is a larger polypeptide.

A third suitable protocol is as follows. This protocol directly detects incorporation of phosphate into substrate. The phosphorylation of myosin regulatory light chain is performed in the buffer containing 50 mM MOPS, pH 7.2, 10 mM MgAcetate, 1 mM DTT, 600 µM CaCl2, $2 \times 10^{-7}$ M calmodulin, 500 µM ATP with 32P labeled gamma ATP, (30ci/mMole) at 25° C. Other forms of gamma-labeled ATP or GTP are also suitable. The final MLCK concentration is 2.8 ng/100 µl. The reaction mixture with myosin regulatory light protein without MLCK is preincubated at 25° C. for 10 minutes before MLCK is added. The assay is started by adding MLCK to the precondition mixture and reaction time is recorded. The phosphorylation is stopped by spotting 20 µl of the reaction mixture each time to Whatman circle filter paper (Grade 3) and dropping the filter paper into cold (4° C.) stop solution with 10% TCA, 8% Napyrophosphate. The filter paper is then washed three times in the wash solution containing 10% TCA, 2% Napyrophosphate. The washed filter paper is rinsed once with 100% alcohol and three times with ether and air dried. The amount of phosphorylated myosin regulatory light chain protein on the filter paper with labeled $^{32}$P ATP can be detected in the scintillation counter.

This protocol has the advantage of providing an alternate approach to quantification of cMLCK activity, one that provides an alternative to immunoassay and does not require specific binding agents such as a phosphospecific antibody. By quantifying the amount of phosphate retained by the filter, the amount of phosphate incorporated into the RLC substrate is readily calculated. Since the enzyme and substrate concentration, ATP concentration, $^{32}$P specific activity and reaction conditions are known, steady-state kinetic parameters such as Vmax (enzyme half-maximal velocity) and Km (substrate concentration at which enzyme velocity is half maximal) are readily calculated once the amount of phosphate retained by each filter is known. See, for example, Chapter 8 in Stryer, Biochemistry 3rd Ed., W.H. Freeman & Co., 1988; Dixon and Webb, Enzymes 3rd Ed., Longmans 1979. The impact of a putative inhibitory or activating compound on the enzyme's maximal velocity, Km, affinity for substrate, and affinity for ATP are also readily determined using the approaches and calculations described in Chapter 8 of Stryer and Dixon and Webb. In this way, a compound can be identified as an inhibitor or activator of cMLCK, and an initial assessment of its relative potency can be determined.

Determining Extent of Substrate Phosphorylation by Immunoassay

Determination of the extent of substrate phosphorylation can also be made by any suitable immunoassay, such as those described in Harlow and Lane, Antibodies: A Laboratory Manual, or Ausubel et al., Current Protocols in Molecular Biology, 1998. These include immunoblotting, immunoprecipitation, ELISA, radioimmunoassay, and immuno-affinity. For example, proteins in the cMLCK assay mixture can be immobilized on any suitable substrate (for example, on nitrocellulose membranes; immobilization in a 6, 12, 24, or 96 well plate, etc.) and the amount of phosphorylated substrate detected.

In one embodiment, phosphorylated substrate are detected using a specific binding agent such as an antibody which specifically detects an RLC, or fragment or variant thereof, after MLCK-mediated phosphorylation. For example, the polyclonal phosphospecific antibody described in Example 6 is a suitable choice. Those skilled in the art recognize that the substrate can be varied, and a broad range of other antibodies can be used. For example, rabbit skeletal muscle RLC can be a suitable substrate for cMLCK, and antibodies could be raised that specifically detect the rabbit RLC phosphoserine residue. Monoclonal antibodies are also suitable.

The phosphospecific binding agent can be labeled in a variety of ways, as described in various references readily available to practitioners in the art (see, for example, Harlow and Lane; Antibodies: A Laboratory Manual; Ausubel et al., Current Protocols in Molecular Biology, 1998). For example, the enzyme is linked to a fluorescent label, or linked to an agent such as digoxigenin or biotin that is readily recognized by a secondary binding agent. Commonly, the phosphospecific binding agent is used as a primary binding agent.

Following binding of the phosphospecific binding agent and appropriate washing, a secondary binding agent capable of binding to the phosphospecific binding agent is used. An example is anti-mouse Fc antibodies, when the phosphospecific binding agent is a mouse monoclonal antibody. The secondary antibody can be conjugated to an enzyme such as alkaline phosphatase or horseradish peroxidase, a fluorescent label, or the like, and detected by spectroscopy, autofluorography, chemiluminescence, etc. as indicated. As another alternative, the secondary antibody can be, for example, an anti-digoxigenin, anti-biotin antibody, anti-DNP antibody, or anti-fluorescein isothiocyanate antibody conjugated to an appropriate label. The choice of secondary antibody depends on the nature of the primary specific binding agent. For example, if the phosphospecific binding agent is a polyclonal antibody conjugated to digoxigenin, an anti-digoxigenin antibody conjugated to alkaline phosphatase or fluorescein isothiocyanate would be an appropriate choice for secondary antibody.

After completing binding of specific binding agents and washing, the amount of phosphospecific antibody bound is determined. Enzyme-conjugated antibodies can be detected by visual inspection of color development, spectroscopy, and chemiluminescence, depending on the reagents used. For example, a bound alkaline phosphatase-conjugated antibody can be detected by chemiluminescence after incubation with ELISA-Light™ (Applied Biosciences) reagent according to the manufacturer's instructions.

Usually, conjugated secondary antibodies and detection kits are obtained commercially from suppliers such as Dako, Applied Biosciences, and Oxford Biomedical Research. These kits are supplied with detailed instructions for use in particular kinds of immunoassays.

Another well-known approach is to immobilize a binding agent capable of binding phosphorylated cMLCK substrate, and contacting the immobilized binding agent with the substrate in solution at the completion of the assay for myosin light chain kinase biological activity.

For example, the antibody-sandwich ELISA described at p. 11-8 and 11-9 of Ausubel et al., Short Protocols in Molecular Biology could be suitably adapted to determining the amount of phosphate incorporated into substrate. A phosphospecific antibody such as that described in Example 6 can be used as the "capture antibody." The capture antibody is bound to the coat wells of an Immulon plate as described in Ausubel et al., and contacted with a solution containing RLC substrate. Phosphorylated RLC is bound, whereas unphosphorylated RLC is not. A secondary antibody in this assay can be a second specific anti-RLC antibody (specifically binding to an epitope other than the phosphorylated serine). Alternatively, the RLC substrate can have an epitope tag such as a FLAG® tag, and the secondary antibody an anti-epitope tag antibody. The secondary antibody can be linked to any suitable detectable label.

Those skilled in the art recognize that when a phosphospecific binding agent is provided, any of a broad range of immunoassays could be readily adapted to detection of substrate phosphorylated by cMLCK The above descriptions are provided by way of example, and are not intended to be limiting.

EXAMPLE 16

Treatment of Subjects with Compounds That Modulate Myosin Phosporylation

Compounds identified as cMLCK modulators in Example 15 are useful therapeutically in the treatment of cardiac dysfunction. Such compounds are, for example, pharmaceuticals, peptides, or antibodies which activate or inhibit cMLCK activity.

Compounds may have similarities to compounds that inhibit the smooth muscle isoform of MLCK These include, for example, K-252a (J. Biol. Chem. 263: 6215, 1988); the benzothiazolesulfonamide derivatives described in U.S. Pat. No. 5,504,098 and PCT publication WO 9214712; naptha-lenesulfonamide derivates such as those described by Hidaka et al., Proc. Natl. Acad. Sci. USA, 78: 4354-4357, 1981; amphipathic calmodulin binding peptides such as those described in U.S. Pat. No. 5,840,697; synthetic peptide inhibitors of smooth muscle myosin light chain kinase, such as those described by Knighton et al., Science 258: 130-135, 1992.

Candidate compounds can enhance cMLCK activity. For example, isoforms of cMLCK with enhanced kinase activity have been identified (see, e.g., Example 3). Moreover, calmodulin-independent variants of cMLCK (containing the catalytic domain [approximately amino acid residues 305-515 in SEQ ID NO: 2], but lacking the calmodulin-binding and autoinhibitory domain [approximately residues 540-590 in SEQ ID NO: 2]; see Ikebe et al., Journal of Biological Chemistry. 262: 13828-34, 1987; Pearson et al., Science 241: 970-973, 1988) can readily be constructed and expressed in baculovirus vectors or in eukaryotic expression vectors or gene therapy vectors. For example, a cDNA encoding amino acid residues 1-520 of cMLCK expresses a cMLCK variant which is constituitively active, that is, active in the absence of calcium-calmodulin. Expression of such cMLCK variants in the heart of a subject would significantly enhance myosin light chain phosphorylation.

Human subjects harboring cMLCK alleles and mutations described in this example, as well as human and non human subjects harboring ELC and RLC mutations, have or are prone to significant cardiac dysfunction. The dysfunction most commonly observed is that of cardiac hypertrophy and diastolic dysfunction. The observed associated defects in contractility are related to stretch activation. The present disclosure reveals that myosin phosphorylation decreases the amplitude of stretch activation, thereby diminishing the contribution of stretch activation to overall cardiac contractility. Thus, mutations of cMLCK or RLC that reduce myosin phosphorylation will enhance the contribution of stretch activation to overall cardiac contractility.

The described mutations that alter myosin phosphorylation point to a intrinsic property which is disclosed herein. The heart tightly coordinates the set of complex movements it performs in a cardiac cycle through myosin phosphorylation. Across the heart, variable levels of RLC phosphorylation diminish or enhance stretch activation in a particular region of the heart, thereby contributing substantially to the global functioning of the heart. For example, it is revealed here in that the apex of the heart has significantly higher levels of myosin phosphorylation than the papillary muscles and mid ventricular cavity. Such differential phosphorylation enables the apex to contract more rapidly, providing a physiologic explanation for the long-standing surgeon's observation that the apex moves more rapidly during contraction than the mid ventricle or the base.

The described mutations also show that is possible for global or regional alterations in normal myosin phosphorylation to disrupt cardiac function, and render the subject susceptible to cardiac hypertrophy, diastolic dysfunction, cardiac failure, and other forms of heart disease. For example, the cMLCK double mutation ala 87 val, ala 95 glu, results in a cMLCK with increased activity, and is associated with a particularly virulent form of hereditary cardiac hypertrophy. Thus, inappropriately enhancing myosin phosphorylation leads to (1) inappropriate decreases in the magnitude of stretch activation in one or more regions of the heart, and (2) inappropriate increases in tension. The result in this particular instance is massive hypertrophy, as the heart seeks to compensate for disputed stretch activation. Such pathologic hypertrophy is unfortunately not compensatory, but in fact significantly worsens the clinical status of the subject.

Even when an obvious phenotype is not associated with a particular mutation, such individuals are believed to have or be prone to cardiac dysfunction. For example, the gly 89 asp cMLCK allele described in Example 3 has an 8% prevalence in African-American populations. African-Americans are known to be disproportionately susceptible to cardiac hypertrophy and diastolic dysfunction, and this predilection can be explained in part by the high prevalence of the cMLCK gly 89 asp allele (and likely other cMLCK mutations) in this population. Since hypertrophy and diastolic dysfunction frequently lead to heart failure, modulation of cMLCK activity represents a novel and potential important new approach preventing hypertrophy and diastolic dysfunction, thereby treating or preventing heart failure.

Moreover, since heart failure from any cause is characterized by systolic dysfunction, diastolic dysfunction, or both, regional or global modulation of cMLCK activity would be an effective approach to therapy regardless of the cause for cardiac dysfunction. Modulation of stretch activation is effective even when cardiac dysfunction is not specifically due to mutations in cMLCK or RLC. For example, by enhancing stretch activation, inhibition of myosin phosphorylation should be an extremely effective approach to cardiac failure. Systolic (contractile) function is significantly enhanced by enhanced stretch activation, whereas diastolic function is also improved, by decreasing the sensitivity of the contractile apparatus to calcium (see Sweeny and Stull, American Journal of Physiology 250: C657-660, 1986; Sweeney and Stull, PNAS 87: 414-418, 1990).

In one embodiment, an agent identified herein as an effective modulator of myosin phosphorylation or cMLCK activity (hereinafter "modulator") is administered to a subject using techniques well-known in the art. A pharmaceutical composition or cMCLK modulatory peptide or antibody of the present invention is combined with a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters.

A pharmaceutically acceptable carrier can contain physiologically acceptable compounds that act, for example, to stabilize the modulator or increase the absorption of the modulator. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration and on the particular physio-chemical characteristics of the specific modulator.

Methods of administering a pharmaceutical are well known in the art. One skilled in the art would know that a pharmaceutical composition comprising a modulator of the present invention can be administered to a subject by various routes including, for example, orally, intravaginally, rectally, or parenterally, such as intravenously, intramuscularly, subcutaneously, intraorbitally, intracapsularly, intraperitoneally, intracistemally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment or powder, or active, for example, using a nasal spray or inhalant. A modulator also can be administered as a topical spray, in which case one component of the composition is an appropriate propellant. The pharmaceutical composition also can be incorporated, if desired, into liposomes, microspheres or other polymer matrices (Gregoriadis, Liposome Technology, Vol. 1, CRC Press, Boca Raton, Fla. (1984), which is incorporated herein by reference). Liposomes, for example, which consist of phospholipids or other lipids, are nontoxic, physiologically acceptable and metabolizable carriers that are relatively simple to make and administer. Administration can be effected continuously or intermittently and will vary with the subject and is dependent on the type of treatment and potency of the modulator used.

In order to modulate the biological activity of a cMLCK, the modulator must be administered in an effective dose, which is termed herein as "pharmaceutically effective amount." The effective dose will, of course, depend on the mode of administration and the relative potency of the modulator. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a cMLCK modulator required to obtain an effective dose in a subject depends on many factors including the age and general health of the subject as well as the route of administration and the number of treatments to be administered. In view of these factors, the skilled artisan would adjust the particular dose so as to obtain an effective dose for modulating cMLCK.

EXAMPLE 17

Genomic Structure of cMLCK

This example presents the twelve exons of cMLCK, together with flanking intronic sequences and primers useful in amplification of segments of the cMLCK gene. Exon sequences are presented in ALL CAPS BOLD font.

Examples of sequences which are useful in amplifying a particular exon are underlined. For exons 2 and 3, two primer pairs are provided. The sense strand is shown in 5'-3' direction. The primer nearer the 5' end is synthesized as shown. The primer nearer the 3' end is synthesized as the reverse complement of the underlined sequence. For example, to amplify Exon 1 and some flanking intronic sequence, an Exemplary Forward primer is: gctagaagacttgagttagacaa (see SEQ ID NO:3); an Exemplary Reverse primer is: catgcaaacaaggctg (that is, the reverse complement of cagccttgtttgcatgtgcacg, see SEQ ID NO:3).

For exon 2, the exemplary primers primer pairs are overlapping, with the two forward primers being aaagg aaaggagggtggatcctgatggtgttctcacctc (see SEQ ID NO:4) and CTGGCCAGGCTAAGATGCAAG (see SEQ ID NO:4). For exon 3, the exemplary primers primer pairs are overlapping, with the two forward primers being cctctgtgttctcaccttctag (see SEQ ID NO:5) and CTGGCCAGGCTAAGATGCAAG (see SEQ ID NO:5).

```
EXON 1 (SEQ ID NO:3)
gactgctcctgagcagccgctggagacagacggcaaccaggttggccctctttgctccaggtacctctctcccctcagtta gcaggctcggcttcctgtctcactgcagccagacgagaggggaaattggacagcctgccacactccactcttgtttctgcagct agaaagacttgagttagacaagcagaagcacacgcctccctacctcATGGCGACAGAAAATGGAGCA GTTGAGCTGGGAATTCAGAACCCATCAACAGgtgccaagctggggcaggagatggaggg aggagcttgggaagggggttttgaatccaggactgggcaaggttccctcagtgggagttctgtgccccagccttgtttgcatg gtgcacg EXON 2 (primer pairs overlap, SEQ ID NO:4)
aaaggagaggtggatcctgatggtgttctcacctctgcagACAAGGCACCTAAAGGTCCCACAGGT

GAAAGACCCCTGGCTGCAGGGAAAGACCCTGGCCCCCCAGACCCAAAG

AAAGCTCCGGATCCACCCACCCTGAAGAAAGATGCCAAAGCCCCTGCC

TCAGAGAAAGGGGATGGTACCCTGGCCCAACCCTCAACTAGCAGCCAA

GGCCCCAAAGGAGAGGGTGACAGGGCGGGGGCCCGCGGAGGGCAG

TGCTGGGCCCCCGGCAGCCCTGCCCCAGCAGACTGCGACACCTGAGAC

CAGCGTCAAGAAGCCCAAGGCTGAGCAGGGAGCCTCAGGCAGCCAGG

ATCCTGGAAAGCCCAGGGTGGGCAAGAAGGCAGCAGAGGGCCAAGCA

GCAGCCAGGAGGGGCTCACCTGCTTTCTGCATAGCCCCAGCTGTCCT

GCCATCATCTCCAGgtgaatatcccctcctgggagtggggagggtcctgtggttctgtccctaggggtcctgc ttaattcccttgt
```

-continued

EXON 3 (primer pairs overlap, SEQ ID NO:5)
gcgggcttca<u>cctctgtgttctcaccttctag</u>TTCTGAGAAGCTGCTGGCCAAGAAGCCCCCA

AGCGAGGCATCAGAGCTCACCTTTGAAGGGGTGCCCATGACCCACAGC

CCCACGGATCCCAGGCCAGCCAAGGCAGAAGAAGGAAAG<u>AACATCCTG</u>

<u>GCAGAGAGCCAG</u>AAGGAAGTGGGAGAGAAAACCCCAGGCCAGG<u>CTGG</u>

<u>CCAGGCTAAGATGCAAG</u>GGGACACCTCGAGGGGATTGAGTTCCAGGC

TGTTCCCTCAGAGAAATCCGAGGTGGGCAGGCCCTCTGTCTCACAGC

CAGGGAGGAGGACTGCTTCCAGATTTTGGgtaggccaggggcaggtgggggctggggctg ctctggggccaggggaggaaggggg<u>ctgtcagtcccaagtctacct</u>

EXON 4 (SEQ ID NO:6)
<u>tggtgccaaggggaatcctcag</u>cagccctggcactgaccatgagggctgtgctctgtccccagATGATTGCCC

GCCACCTCCGGCCCCCTTCCCTCACCGCATGGTGGAGCTGAGGACCGG

GAATGTCAGCAGTGAATTCAGTATGAACTCCAAGGAGGCGCTCGGAGG gtgagatctgggaccccagctgggcact<u>catggacagagagcacaccg</u>

EXON 5 (SEQ ID NO:7)
<u>cttggggtcccctaacttacag</u>cctcttctctttccagTGGCAAGTTTGGGGCAGTCTGTACCTGC

ATGGAGAAAGCCACAGGCCTCAAGCTGGCAGCCAAGGTCATCAAGAAA

CAGACTCCCAAAGACAAGgtagtgaggttgcgggggtggtggctgcccaggatggggagggatcctt ggagtagggcacctctcgcctccctc<u>caccagcagctgctgaacctg</u>

EXON 6 (SEQ ID NO:8)
<u>gtaccctttacttccctggtc</u>cccagGAAATGGTGTTGCTGGAGATTGAGGTCATGAACC

AGCTGAACCACCGCAATCTGATCCAGCTGTATGCAGCCATCGAGACTC

CGCATGAGATCGTCCTGTTCATGGAGTAgtgagtggccgaagtagtggtaggggctgggtgg gggtaccac<u>caggcacggagcaagccgtgga</u>

EXON 7 (SEQ ID NO:9)
<u>taccaccaggcacggagcaag</u>ccgtggagggggtctgtgcacgcaCATCGAGGGCGGAGAGCTCTT

CGAGAGGATTGTGGATGAGGACTACCATCTGACCGAGGTGGACACCAT

GGTGTTTGTCAGGCAGATCTGTGACGGGATCCTCTTCATGCACAAGAT

GAGGGTTTTGCACCTGGACCTCAAGgta<u>accagactggggcctcctgggaag</u>

EXON 8 (SEQ ID NO:10)
<u>tgcagaggcccacccaggcca</u>ccccctttctcctcagCCAGAGAACATCCTGTGTGTCAACACC ACCGGGCATTTGGTGAAGATCATTGACTTTGGCCTGGCACGGAGgtaccac ctgggtgggtgggagggcaagacaagcctct<u>gagttggcaggggcagggtg</u>

EXON 9 (SEQ ID NO:11)
<u>ggactgtgctctcagcccttg</u>gtctcaccccaggGTATAACCCCAACGAGAAGCTGAAGGTG

AACTTTGGGACCCCAGAGTTCCTGTCACCTGAGGTGGTGAATTATGACC

AAATCTCCGATAAGACAGACATGTGGAGTATGGGGGTGATCACCTACA

TGCTgtgagcacccaggagg<u>gtcgtgtttatgggggttggt</u>

EXON 10 (SEQ ID NO:12)
<u>cctccaatctcacctccctgc</u>cccctgctatcccctccctctagGCTGAGCGGCCTCTCCCCCTTCCT

GGGAGATGATGACACAGAGACCCTAAACAACGTTCTATCTGGCAACTG

GTACTTTGATGAAGAGACCTTTGAGGCCGTATCAGACGAGGCCAAAGA

CTTTGTCTCCAACCTCATCGTGAAGGACCAGAGgtgaggctcaccccagaacctgaact gtatgtgtgcaagcttag<u>tgtgtctgagtgctggcagg</u>

-continued

EXON 11 (SEQ ID NO:13)
ccacgtcaccatgctgcctctccccccaGGCCCGGATGAACGCTGCCCAGTGTCTCGCCC

ATCCCTGGCTCAACAACCTGGCGGAGAAAGCCAAACGCTGTAACCGAC

GCCTTAAGTCCCAGATCTTGCTTAAGAAATACCTCATGAAGAGGCGCTG

GAAGgtaccgctggattcggggtggggagggagggcttgctagtgggaagagctcctggtgccagatcccagc

EXON 12 (SEQ ID NO:14)
ccctgccctggtgttgactgggactccctctcttctgccctctagAAAAACTTCATTGCTGTCAGCGCT

GCCAACCGCTTCAAGAAGATCAGCAGCTCGGGGGCACTGATGGCTCTG

GGGGTCTGAgccctgggcgcagctgaagcctggacgcagccacacagtgg

EXAMPLE 18

Enzyme Kinetics of the Mutant MLCK

In order to further investigate the effect of the mutant kinase, both entire wild type and mutant human skeletal/cardiac MLCK proteins (with amino-terminal FLAG® tags) were expressed in baculoviral systems and affinity purified. Human cardiac RLC, human ventricular ELC and a fragment of the β-myosin heavy chain light chain binding region (aa778-840) were co-expressed. Affinity column purification utilizing an expressed FLAG tag placed at the carboxy-terminal end of the heavy chain fragment yielded a purified complex of the 2 light chains and light chain binding fragment. This complex was used as substrate in the kinetic studies of the expressed wild type and mutant kinases. A double reciprocal plot of 1/v vs. 1/[S] comparing the mutant and wild type MLCK was created. The $V_{max}$ of the mutant is almost double that of the wild-type MLCK (216.±31 vs. 115±15 pmoles min$^{-1}$ ng$^{-1}$ respectively), while the $K_m$ of the mutant is also significantly greater than the wild type (17.0±4.6 vs. 6.0±1.8 µM respectively). At physiologic concentrations of light chain (~300 µM), differences in $V_{max}$ dominate the rate of RLC phosphorylation.

EXAMPLE 19

Detailed Investigation of Muscle Strain Pattern in Left Ventricle with Non-Invasive Phase-Labeled MRI Techniques (metaDENSE)

A differential pattern of myosin RLC phosphorylation from epicardium to endocardium across the ventricular wall is disclosed herein. This, together with the biophysical changes observed in single fiber studies, predicts an effect on the global pattern of cardiac contraction In order to study the pattern of contraction in the normal human heart recent developments in phase-labeled MRI motion tracking were utilized that allow detailed mapping of muscle strain and torsion distribution in the left ventricular wall (Aletras et al., 1999; Aletras, 2000; Callaghan, 1991). One such technique, metaDENSE, has been optimized to map the displacement field of the human heart at 2.8 mm resolution during a breath-hold of 14 heartbeats, over the entire systolic or diastolic period. The spatial resolution of this technique is sufficient to clearly show changes in the contractile strain and torsion of the muscle across the wall. The left ventricle undergoes torsion around its long axis during systolic contraction, i.e., the apex rotates relative to the base. Recoil occurs in the diastolic period. The direction of torsion is consistent with the helical arrangement of the epicardial muscle fibers but counters the helicity of the endocardial fibers. Therefore, the epicardium is thought to produce the torsion during systole.

High resolution torsion measurements with metaDENSE showed 50% to 70% increase in normalized torsion from the epicardial to endocardial border (manuscript in preparation, HW). A color-coded distribution of the rotation of the myocardial wall around the LV center in a slice of the left ventricle perpendicular to its long axis, about one-fourth the LV length from the apex was generated, derived from a set of metaDENSE images that encode the wall motion over the entire systolic period. The endocardium was darker in color than the epicardium, indicating an increase in the angle of rotation from the epicardial border to the endocardial border. This phenomenon has also been observed with MR tagging studies at lower spatial resolution (Buchalter et al., 1990; Maier et al., 1992; Young et al., 1994).

Having illustrated and described the principles of isolating the human cardiac myosin light chain kinase cDNA and its corresponding genomic gene, the protein and modes of use of these biological molecules, it should be apparent to one skilled in the art that the invention can be modified in arrangement and detail without departing from such principles. The scope of the invention is defined by the following claims. We therefore claim as our invention all that comes within the scope and spirit of these claims.

We claim:

1. An isolated cardiac myosin light chain kinase protein comprising:
   (a) the amino acid sequence set forth in SEQ ID NO: 2; or
   (b) the amino acid sequence with at least 98% sequence identity to the amino acid sequence set forth in SEQ ID NO: 2, wherein the protein has cardiac myosin light chain kinase activity.

2. A method of screening for an agent that modulates phosphorylation of a cardiac myosin light chain kinase protein, the method comprising:

a) incubating the agent at a concentration with the isolated cardiac myosin light chain kinase protein of claim 1 and a cardiac myosin light chain kinase substrate, under conditions that permit phosphorylation of the substrate by the cardiac myosin light chain kinase protein;
   b) detecting phosphorylation of the substrate;
   c) incubating the agent at a different concentration with the isolated cardiac myosin light chain kinase protein and the substrate, under conditions that permit phosphorylation of the substrate by the cardiac myosin light chain kinase protein;

d) detecting phosphorylation of the substrate in the presence of the different concentration of the agent; and e) comparing phosphorylation of the substrate obtained after incubation with the concentration of the agent, with phosphorylation of the polypeptide substrate obtained after incubation with the different concentration of the agent, thereby determining if the agent modulates phosphorylation of the cardiac myosin light chain kinase protein.

3. The method of claim 2, wherein phosphorylation of the substrate is detected by:

immobilizing the substrate;

contacting the immobilized substrate with a primary antibody which specifically binds to a phosphorylated form of the substrate;

removing any primary antibody not specifically bound to the immobilized substrate; and detecting the presence of primary antibody bound to the immobilized substrate.

4. The method of claim 3, wherein detecting the presence of primary antibody bound to the immobilized substrate comprises:

contacting the primary antibody with a secondary antibody, wherein the secondary antibody comprises a detectable label;

removing any secondary antibody not specifically bound to the primary antibody; and detecting the presence of the secondary antibody bound to the primary antibody.

5. The method of claim 2, further comprising:

incubating the immobilized substrate and the isolated cardiac myosin light chain kinase protein with ATP comprising a label; and detecting phosphorylation of the substrate by detecting the label incorporated into the substrate.

6. The isolated cardiac myosin light chain kinase protein of claim 1, wherein the protein comprises the amino acid sequence set forth in SEQ ID NO: 2, wherein alanine is substituted for glutamine at position 89.

7. The isolated cardiac myosin light chain kinase protein of claim 1, wherein the protein comprises the amino acid sequence set forth in SEQ ID NO: 2, wherein proline is substituted for alanine at position 144.

8. The isolated cardiac myosin light chain kinase protein of claim 1, wherein the protein comprises the amino acid sequence set forth in SEQ ID NO: 2.

9. The isolated cardiac myosin light chain kinase protein of claim 1, wherein the protein is encoded by a nucleic acid sequence at least 98% identical to the nucleic acid sequence set forth in SEQ ID NO: 1, wherein the protein has cardiac myosin light chain kinase activity.

10. The isolated cardiac myosin light chain kinase protein of claim 1, wherein the protein is encoded by a nucleic acid molecule comprising the nucleic acid sequence set forth in SEQ ID NO: 1 or a degenerate variant of the nucleic acid sequence set forth in SEQ ID NO: 1.

* * * * *